(12) United States Patent
Li et al.

(10) Patent No.: US 12,428,437 B2
(45) Date of Patent: Sep. 30, 2025

(54) METAL COMPLEX AND APPLICATION THEREOF

(71) Applicant: GUANGDONG AGLAIA OPTOELECTRONIC MATERIALS CO., LTD, Guangdong (CN)

(72) Inventors: Huiyang Li, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 772 days.

(21) Appl. No.: 17/776,974

(22) PCT Filed: Sep. 19, 2020

(86) PCT No.: PCT/CN2020/116337
§ 371 (c)(1),
(2) Date: May 13, 2022

(87) PCT Pub. No.: WO2021/120741
PCT Pub. Date: Jun. 24, 2021

(65) Prior Publication Data
US 2022/0411452 A1    Dec. 29, 2022

(30) Foreign Application Priority Data

Dec. 16, 2019 (CN) .......................... 201911291180.2

(51) Int. Cl.
*C07F 15/00* (2006.01)
*H01L 51/00* (2006.01)
(Continued)

(52) U.S. Cl.
CPC ......... *C07F 15/0086* (2013.01); *H10K 50/16* (2023.02); *H10K 85/346* (2023.02)

(58) Field of Classification Search
None
See application file for complete search history.

(56) References Cited

U.S. PATENT DOCUMENTS

2006/0073359 A1    4/2006   Ise et al.
2006/0202197 A1    9/2006   Nakayama et al.
2007/0082284 A1    4/2007   Stoessel et al.

FOREIGN PATENT DOCUMENTS

| CN | 1894269 A | 1/2007 |
|----|-----------|--------|
| EP | 2551274 A1 | 1/2013 |
| WO | 2019144845 A1 | 8/2019 |

*Primary Examiner* — Jay Yang
(74) *Attorney, Agent, or Firm* — Maschoff Brennan

(57) ABSTRACT

The present invention relates to a metal complex having a structure of chemical formula (I). The metal complex is applied to an organic light-emitting device which emits deep red or near-infrared light, and shows a lower driving voltage and higher luminous efficiency, and has greatly prolonged service life. Therefore, the metal complex has the potential of being applied in the field of organic light-emitting devices. Also provided is an organic light-emitting device, including a cathode, an anode, and an organic layer. The organic layer is one or more of a hole injection layer, a hole transport layer, a light-emitting layer, a hole blocking layer, an electron transport layer, and an electron injection layer; and at least one layer in the organic layer contains the compound of structural formula (I).

(Continued)

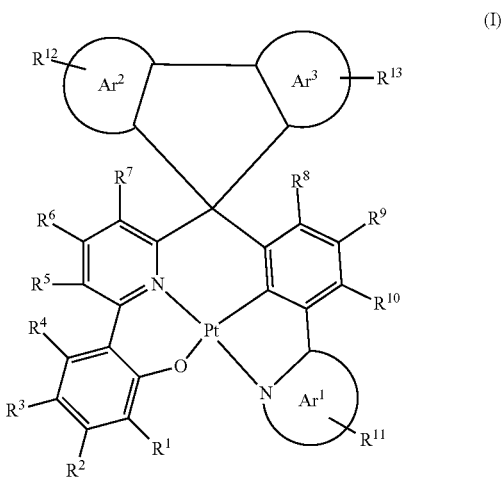
(I)
20 Claims, 1 Drawing Sheet
(51) Int. Cl.
    *H01L 51/50*     (2006.01)
    *H10K 50/16*     (2023.01)
    *H10K 85/30*     (2023.01)

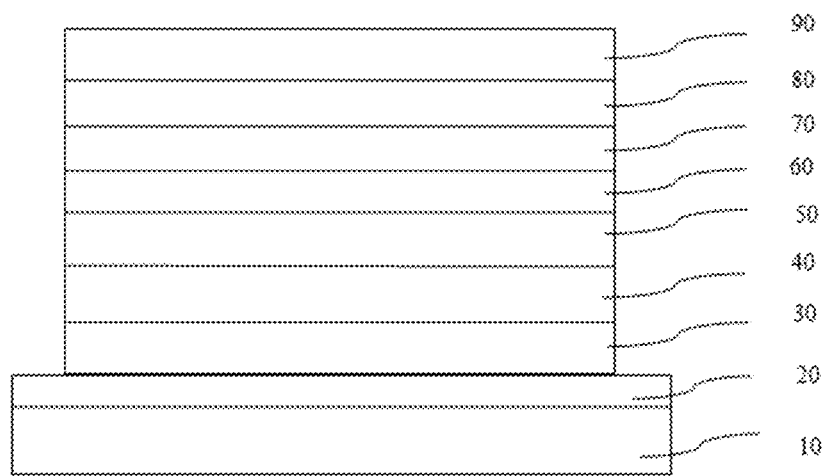

METAL COMPLEX AND APPLICATION THEREOF

TECHNICAL FIELD

The present invention relates to the technical field of organic light-emitting materials, and in particular to a metal compound and an application thereof in an organic light emitting device as a light-emitting material.

BACKGROUND

Organic optoelectronic devices include but not limited to the following types: organic light-emitting devices (OLEDs), organic thin film transistors (OTFTs), organic photovoltaics (OPVs), luminescent electrochemical cells (LECs) and chemical sensors.

In recent years, as a kind of lighting and display technology having great application prospect, OLEDs have been widely concerned in academic circle and industrial circle. OLEDs devices are featured by self-illumination, wide viewing angle, short response time and preparation of flexible devices to be a promising candidate in the next generation of display and lighting technology. But the current OLEDs have the problems such as, low efficiency and short service life and thus, are to further studied by people.

The early-stage fluorescent OLEDs only utilize singlet state for light emission usually; and the triplet exciton produced in the device cannot be effectively utilized and return to the ground state in a non-radiative way. Therefore, the quantum yield of fluorescent OLEDs is comparatively low, thus limiting the promotion and use of the OLEDs. In 1998, CHE Chi-Ming, et al. of University of Hong Kong reported the electrophosphorescence phenomenon for the first time. In the same year, Thompson, et al. used a transition metal complex as a light-emitting material to prepare phosphorescent OLEDs. Phosphorescent OLEDs can utilize singlet state and triplet exciton to emit light simultaneously to achieve 100% internal quantum efficiency, which greatly promotes the commercialization process of OLEDs. The control of color emitted by OLEDs can be achieved by the structural design of the light-emitting materials. OLEDs may include a light-emitting layer or a plurality of light-emitting layers to achieve the required spectrum. At present, green, yellow and red phosphorescent materials have been put into commercial application. Commercialized OLED displays achieve full-color display usually by matching blue fluorescence with yellow, or green and red phosphorescence. Currently, the industrial circle is in urgent need of a light-emitting material having more saturated luminescence spectrum, higher efficiency and longer service life.

Metal complex light-emitting materials have been applied in industry; but in the aspect of performance, such as color saturation and service life still cannot be satisfactory. The present invention provides a series of metal complexes; it has been found by researches that such kind of metal complex can emit red to near-infrared light. It has been found by further study that such kind of complex further has the property of aggregation-induced emission enhancement.

SUMMARY

Directed to the above problems in the prior art, the present invention provides a metal complex light-emitting material; the material is applied in an organic light-emitting device to show good photoelectrical properties and service life. The present invention further provides a light-emitting device, and the device includes the metal complex of the present invention.

An organic light-emitting device, is a compound having a structure as shown in Formula (I):

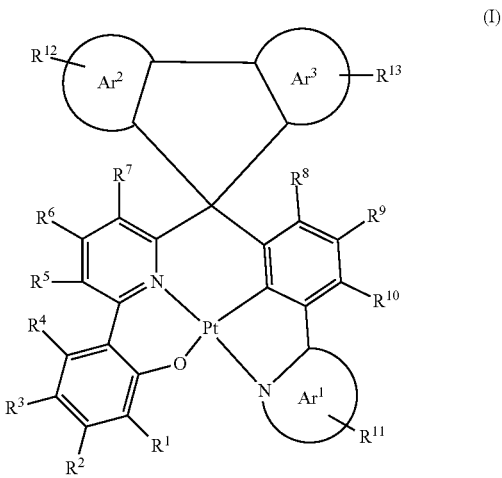

(I)

where:
$R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from: hydrogen, deuterium, halogen, substituted or unsubstituted alkyl having 1-20 carbon atoms, substituted or unsubstituted cycloalkyl having 3-20 carbon atoms, substituted or unsubstituted alkoxy having 1-20 carbon atoms, substituted or unsubstituted aryl having 6-30 carbon atoms, and substituted or unsubstituted heteroaryl having 3-30 carbon atoms or cyano;

$Ar^1$ is a heteroaromatic group containing at least two N atoms and 3-30 carbon atoms; $Ar^2$ and $Ar^3$ are each independently selected from an aromatic group or a heteroaromatic group having 3-30 carbon atoms; heteroatom in the heteroaromatic group is selected from atoms N, S, and O;

and where the substitution refers to a substitution by deuterium, halogen or alkyl having 1-8 carbon atoms.

In the general formula (I), $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from: hydrogen, deuterium, halogen, substituted or unsubstituted alkyl having 1-6 carbon atoms, substituted or unsubstituted cycloalkyl having 3-6 carbon atoms, substituted or unsubstituted alkoxy having 1-6 carbon atoms, substituted or unsubstituted aryl having 6-12 carbon atoms, and substituted or unsubstituted heteroaryl having 3-12 carbon atoms or cyano;

$Ar^1$ is a heteroaromatic group containing 2-4 heteroatoms and 3-12 carbon atoms; $Ar^2$ and $Ar^3$ are each independently selected from an aromatic group or a heteroaromatic group having 3-12 carbon atoms; heteroatom in the heteroaromatic group is selected from atoms N, S, O;

and where the substitution refers to a substitution by deuterium or alkyl having 1-4 carbon atoms.

In the general formula (I), $R^1$, $R^2$, $R^3$, $R^4$, $R^5$, $R^6$, $R^7$, $R^8$, $R^9$, $R^{10}$, $R^{11}$, $R^{12}$, and $R^{13}$ are further respectively selected from: hydrogen, deuterium, substituted or unsubstituted alkyl having 1-4 carbon atoms, substituted or unsubstituted cycloalkyl having 3-6 carbon atoms; $Ar^2$ and $Ar^3$ are each independently selected from an aromatic group or a heteroaromatic group having 5-10 carbon atoms.
In the general formula (I), Ar¹ is preferably selected from the following aromatic structures:
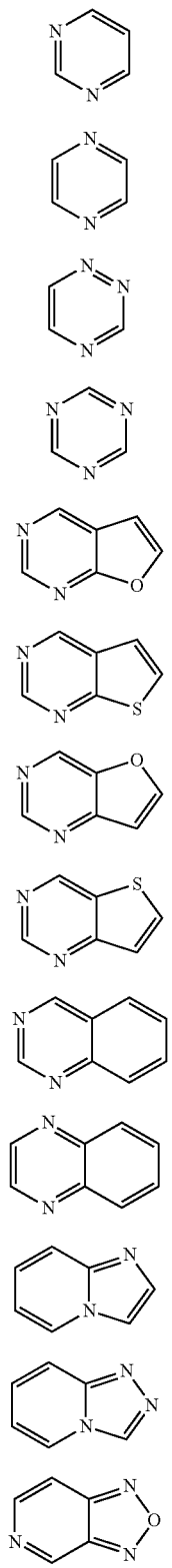
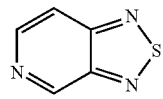
HA14
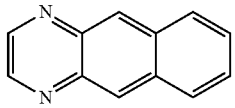
HA15
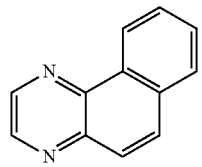
HA16
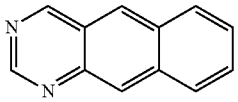
HA17
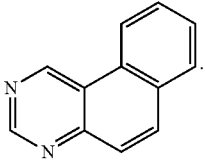
HA18
In the general formula (I), Ar¹ is further preferably selected from the following aromatic structures:
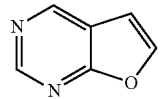
HA5
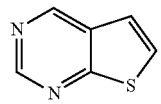
HA6
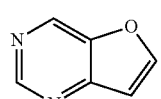
HA7
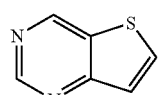
HA8
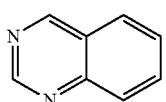
HA9
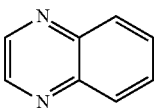
HA10

HA11 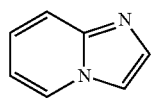

HA12 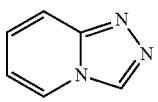

HA13 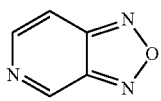

HA14 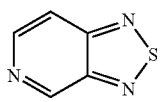

HA15 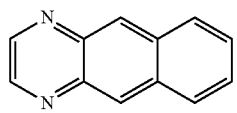

HA16 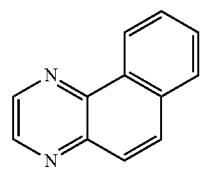

HA17 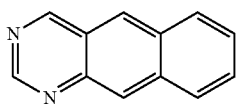

HA18 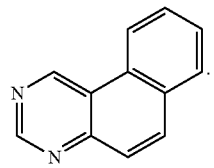

In the general formula (I), preferably, $Ar^2$ and $Ar^3$ are the same aromatic group.

In the general formula (I), preferably, $Ar^2$ and $Ar^3$ are respectively selected from a benzene or naphthalene unit Preferably, $R^1$, $R^2$, $R^3$, $R^4$, $R^5$, $R^6$, $R^7$, $R^8$, $R^9$ and $R^{10}$ are hydrogen.

Examples of the metal complex according to the present invention are listed below, but not limited to the structures listed:

1 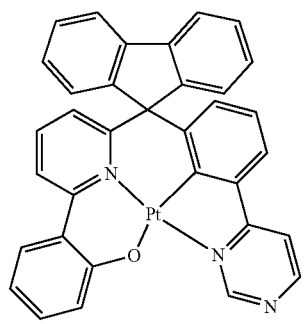

2 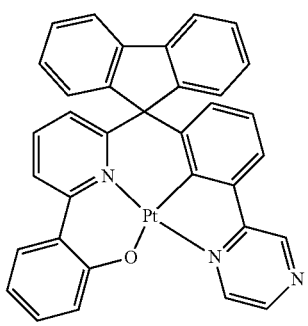

3 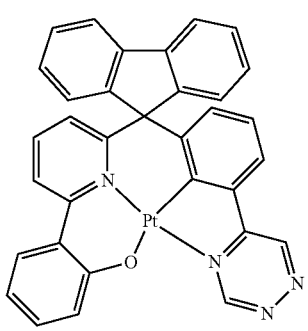

4 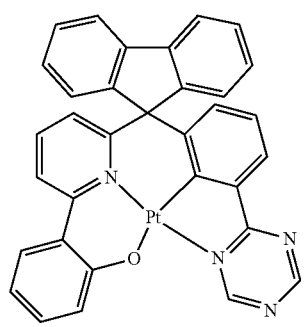

5 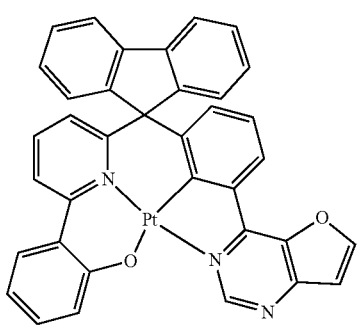

6
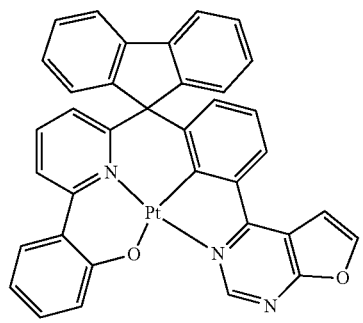
7
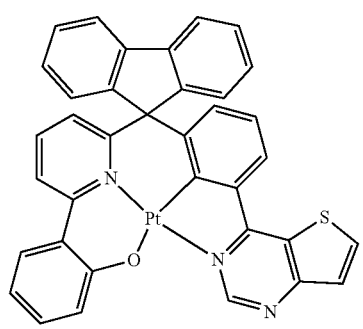
8
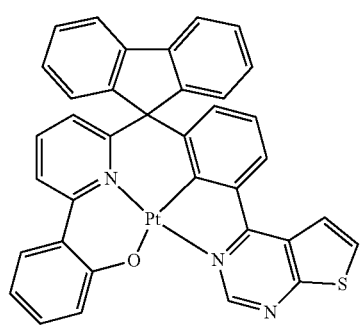
9
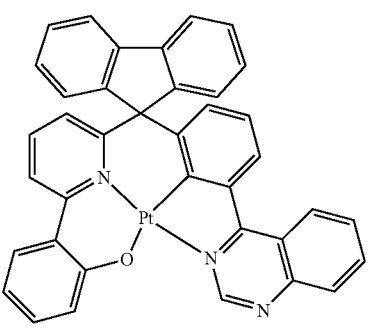
10
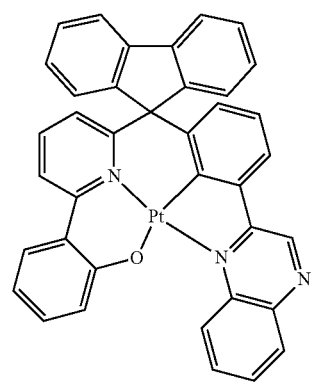
11
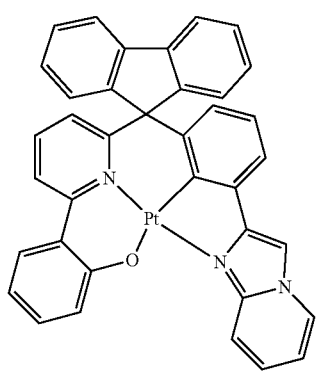
12
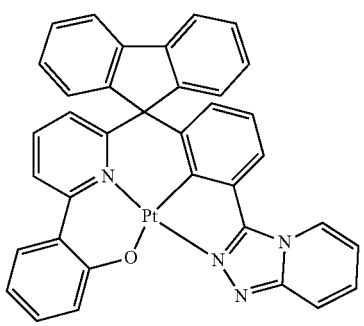
13
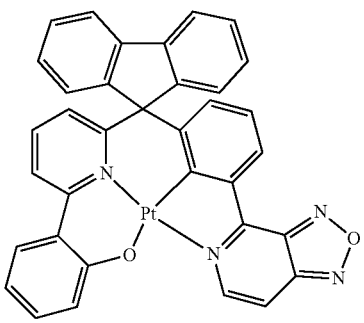

14
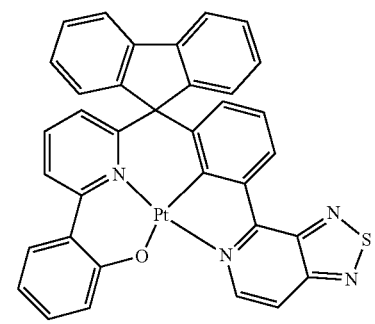
15
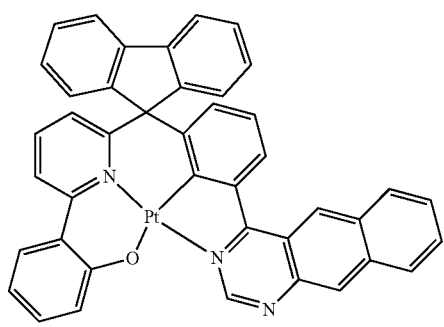
16
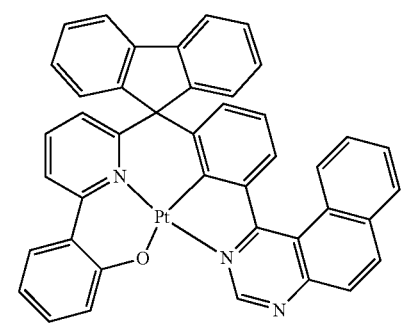
17
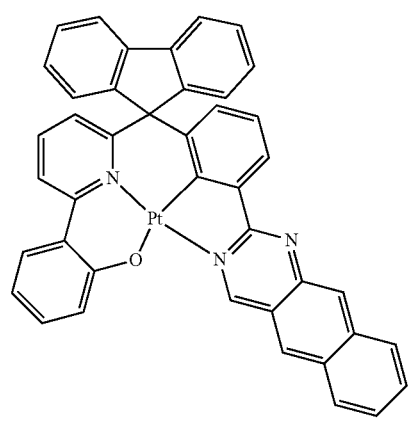
18
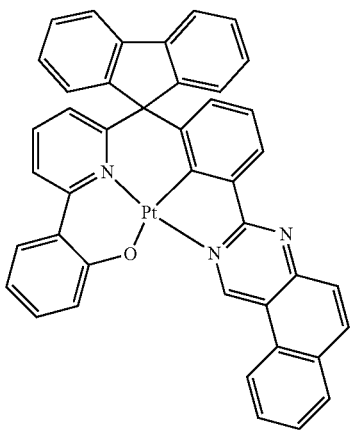
19
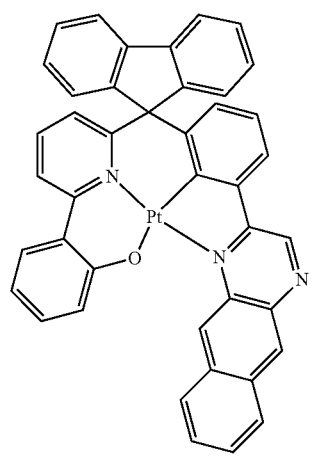
20
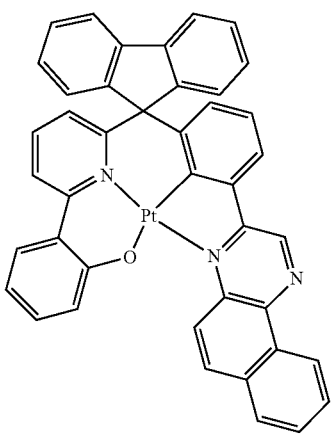
21
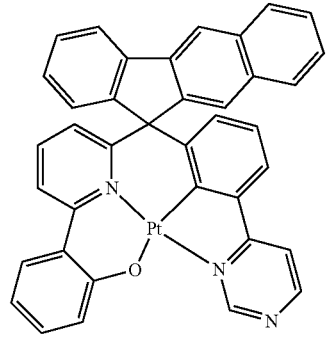

11
-continued
22
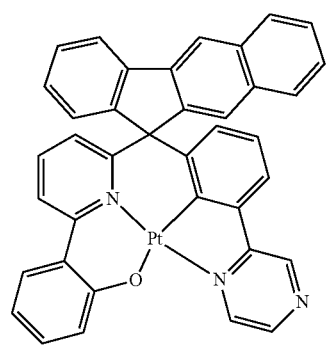
23
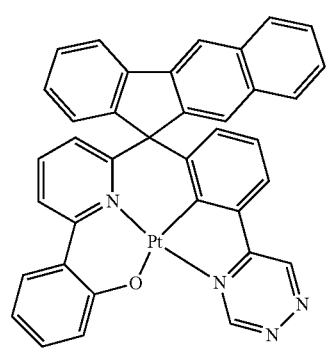
24
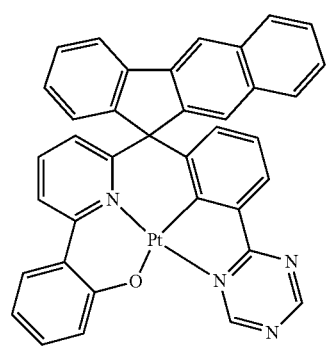
25
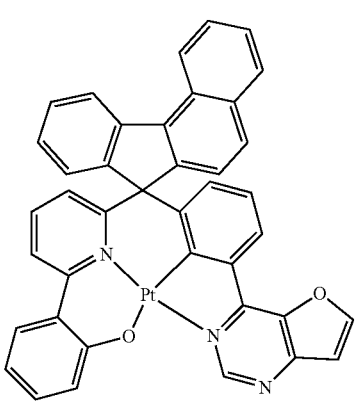
12
-continued
26
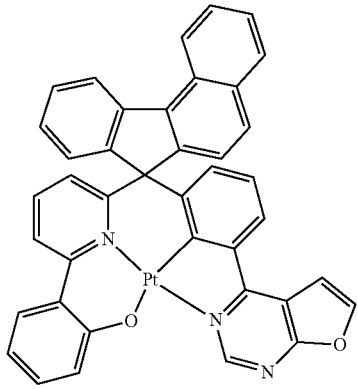
27
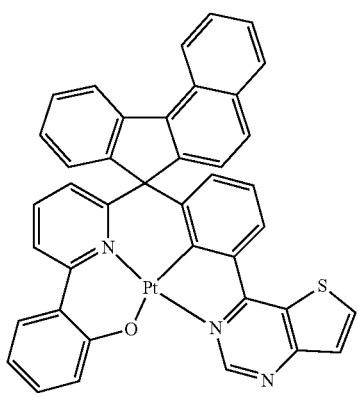
28
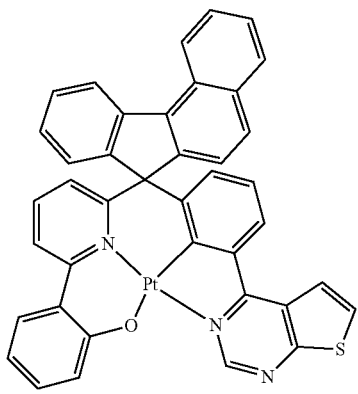
29
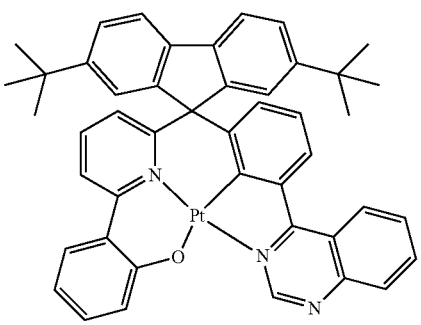

-continued
30
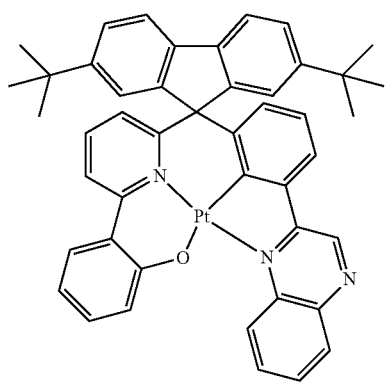
31
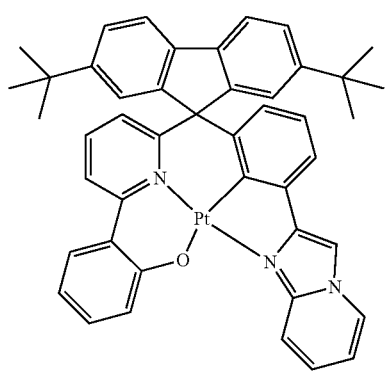
32
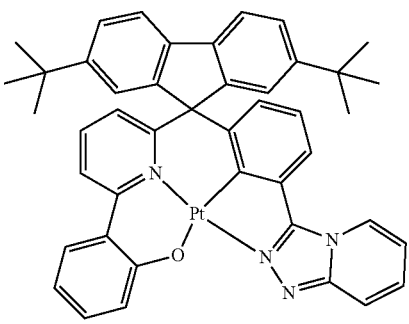
33
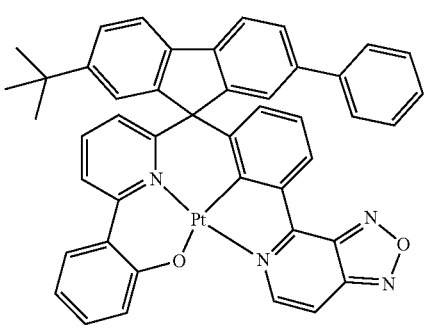
-continued
34
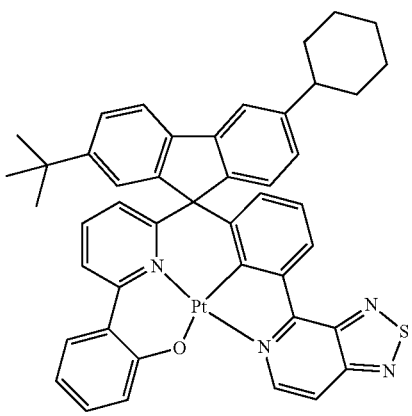
35
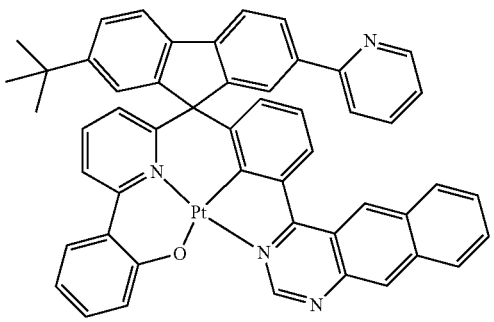
36
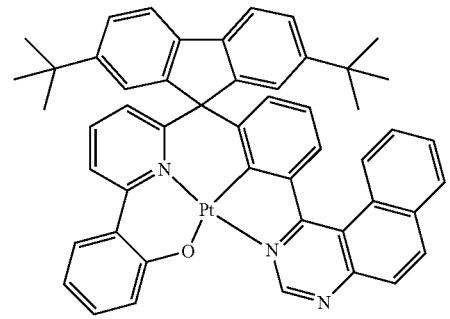
37
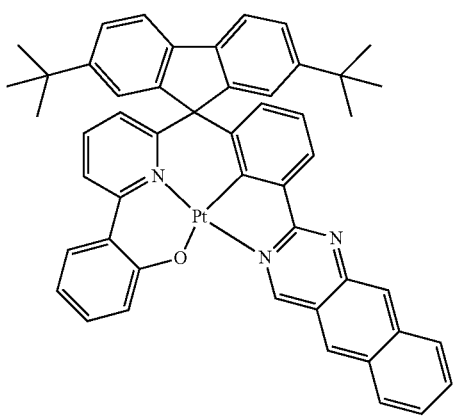

38
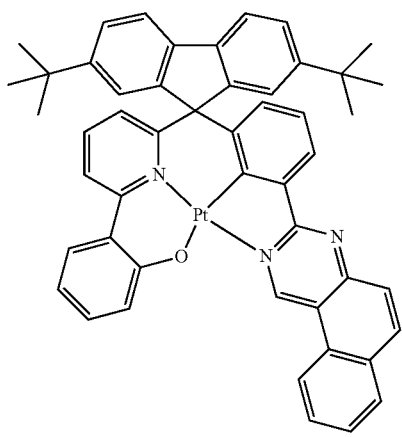
39
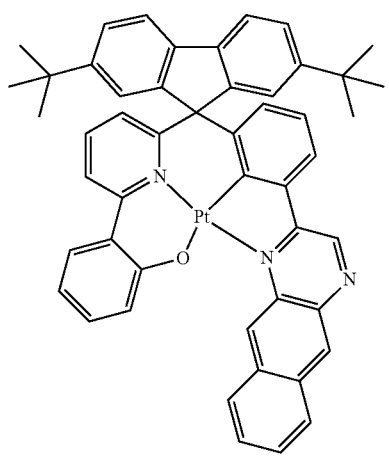
40
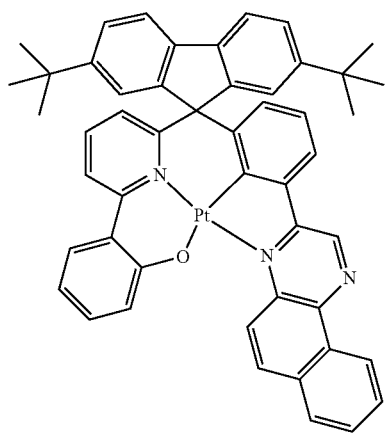
41
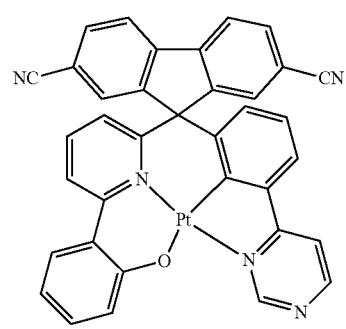
42
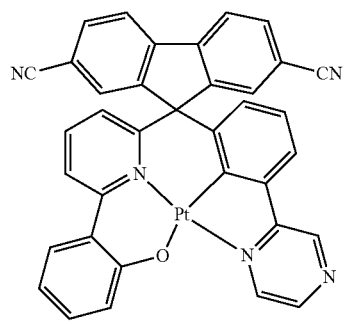
43
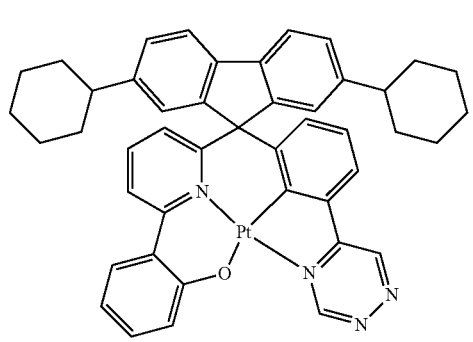
44
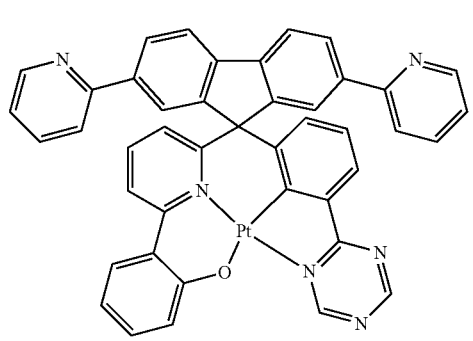
45
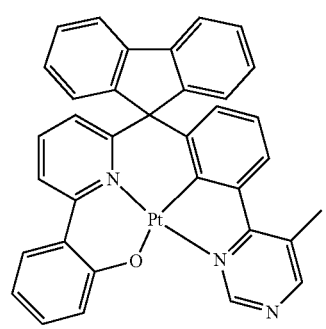

46
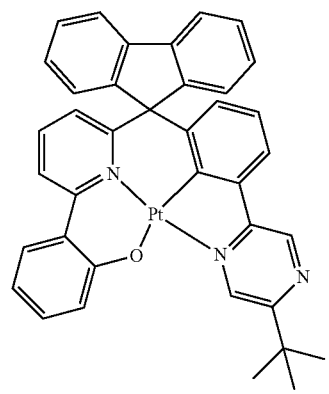
47
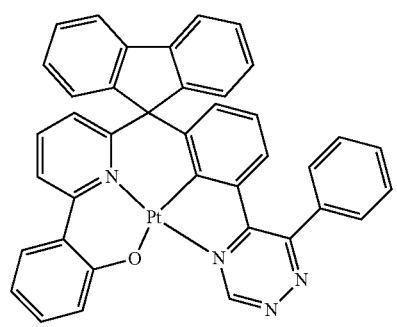
48
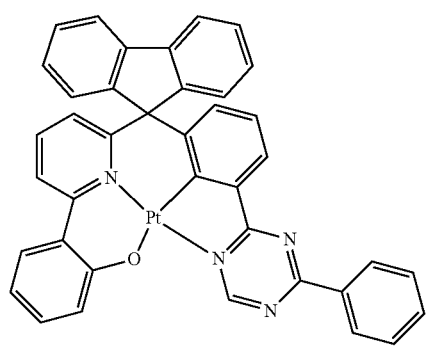
49
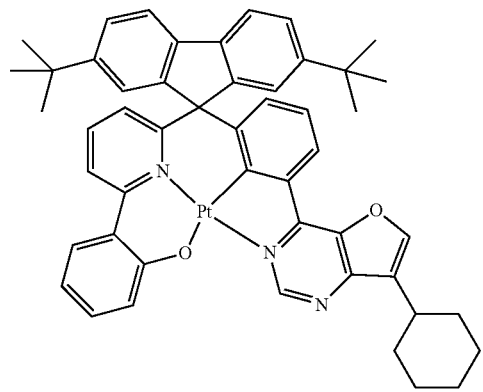
50
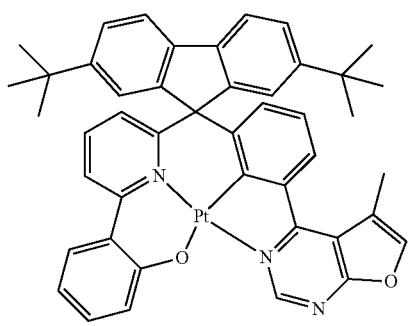
51
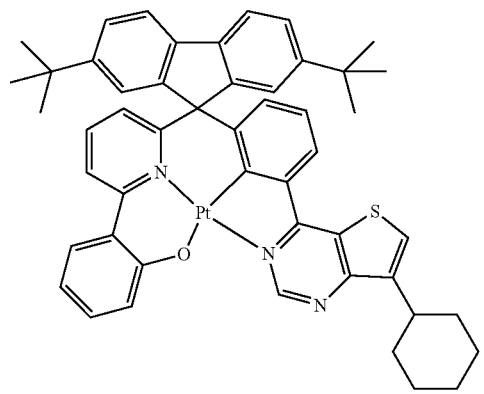
52
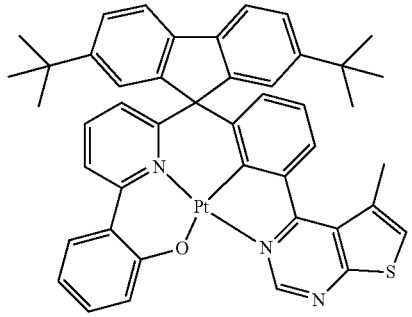
53
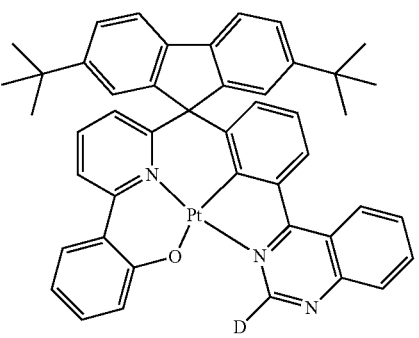

-continued
54
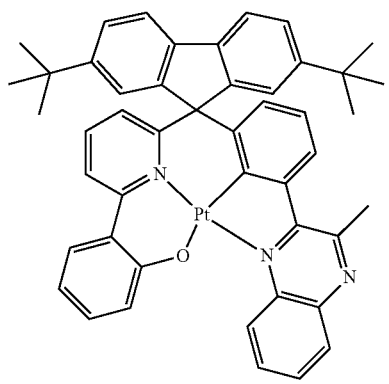
55
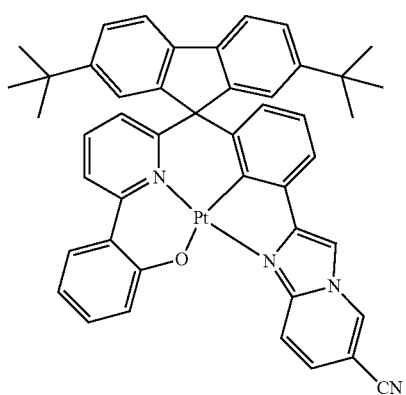
56
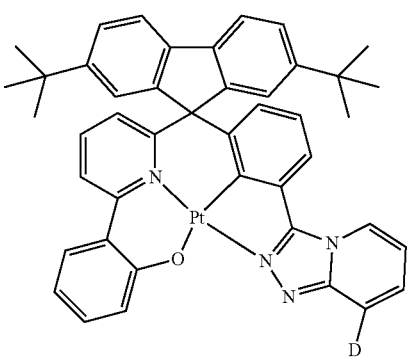
57
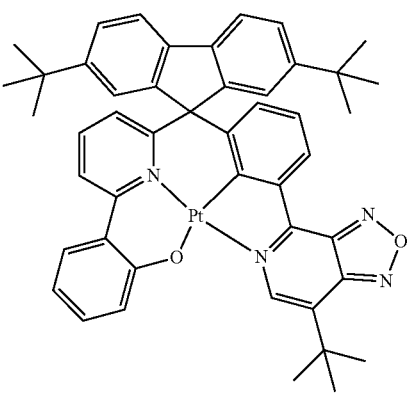
-continued
58
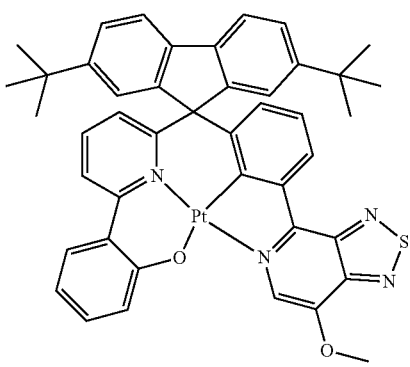
59
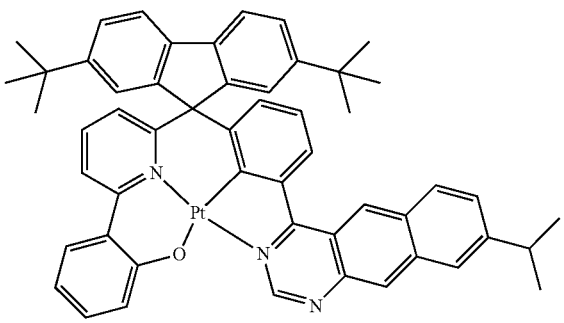
60
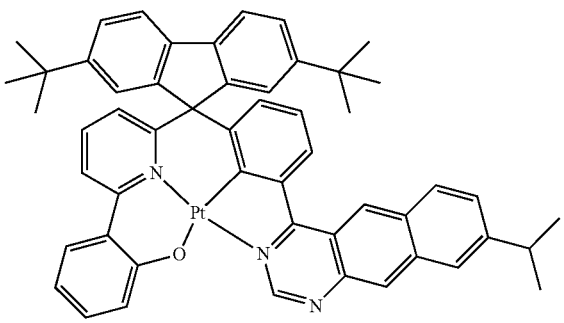
61
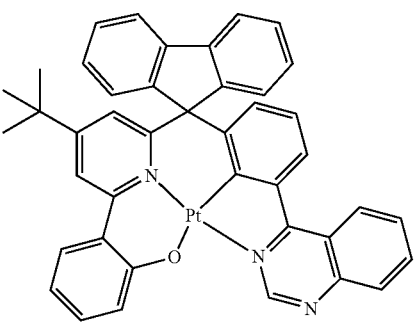

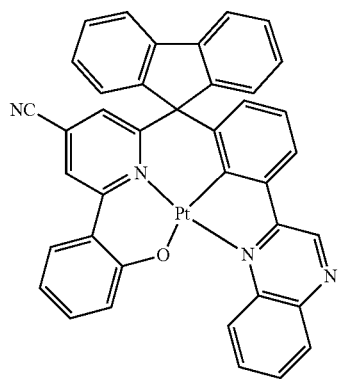
62
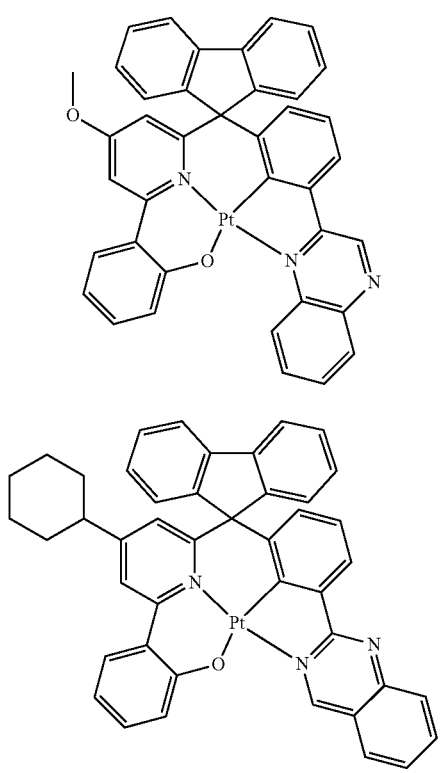
63
64
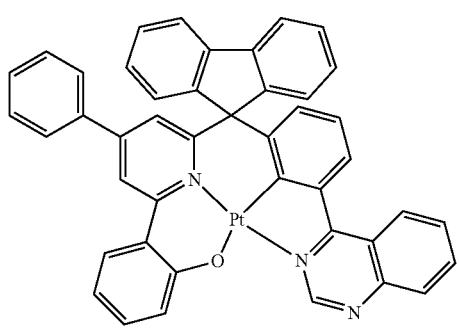
65
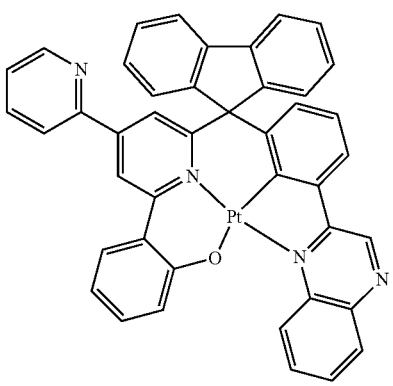
66
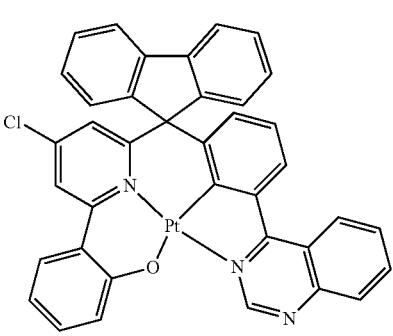
67
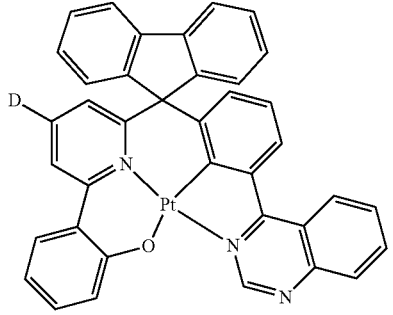
68
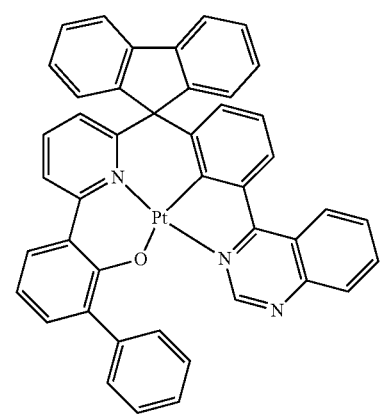
69

-continued
70
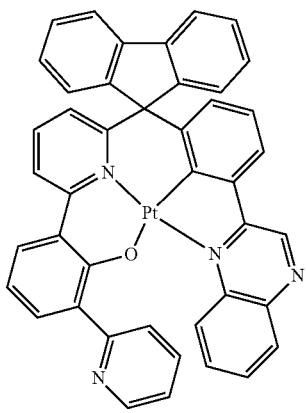
71
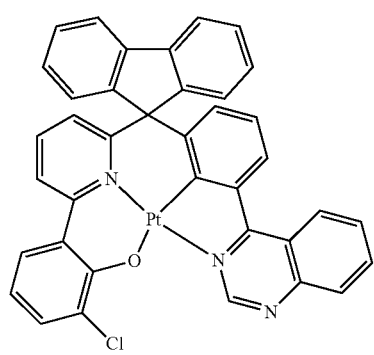
72
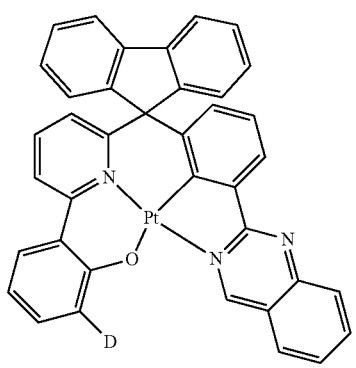
73
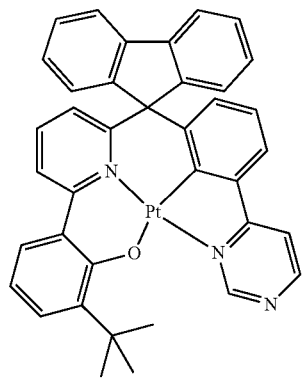
-continued
74
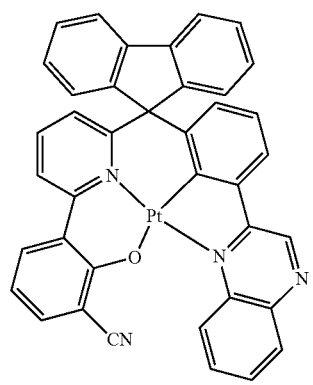
75
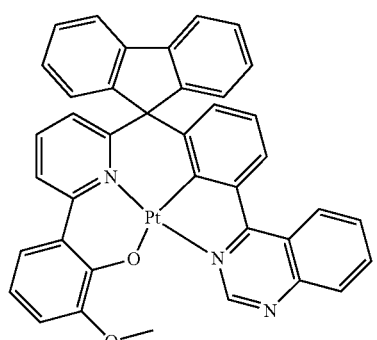
76
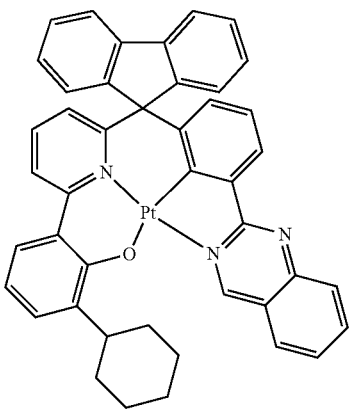
77
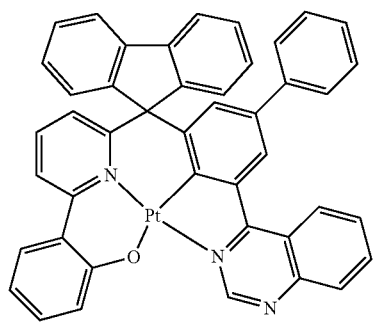

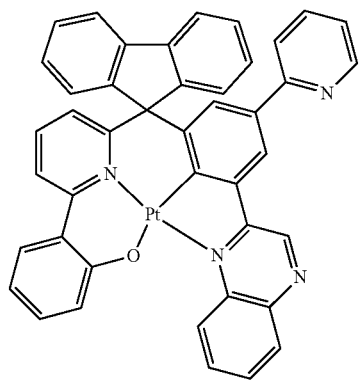
78
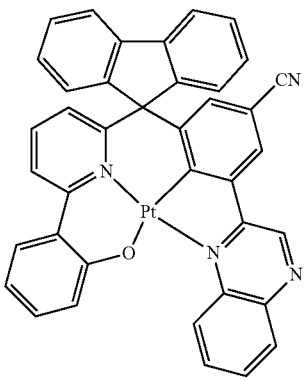
82
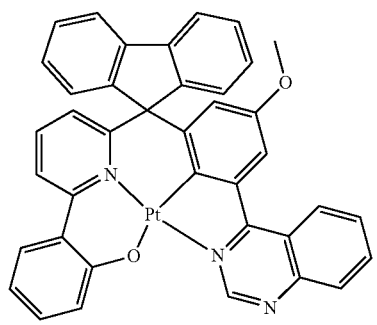
83
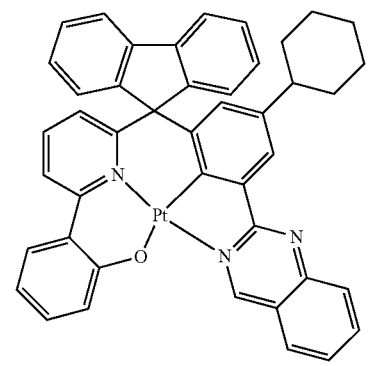
84
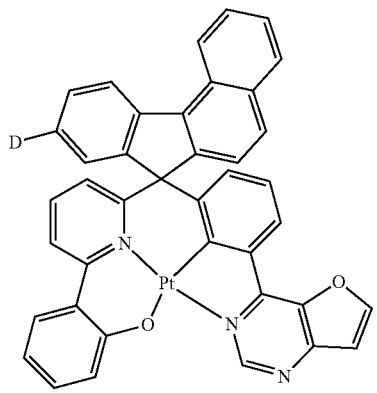
85

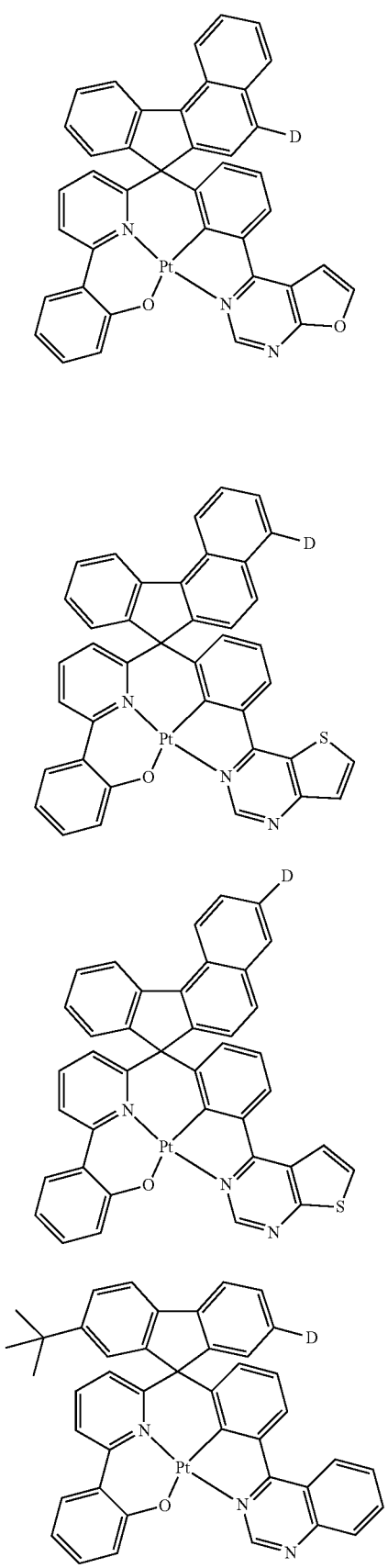
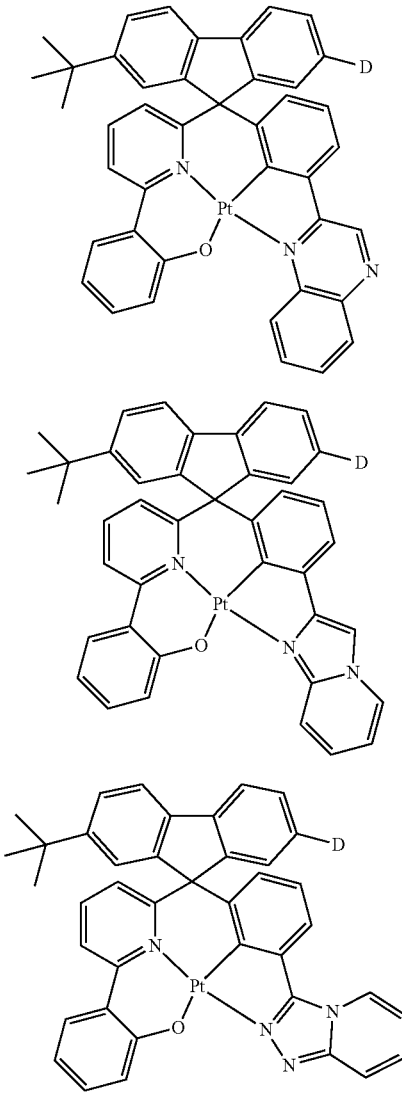
A precursor of the above compound, namely, a ligand, has a structural formula below:
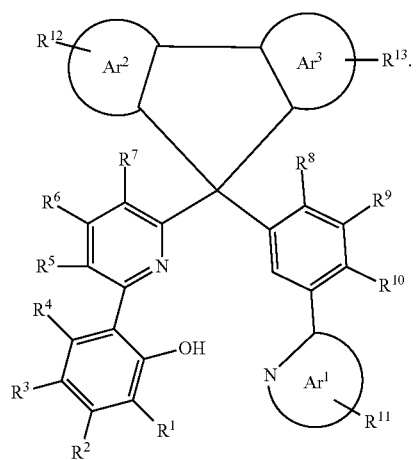

The metal complex light-emitting material of the present invention is applied to a light-emitting device to obtain dark red to near infrared color; the emission wavelength ranges from 620 nm to 1000 nm, preferably, 630 nm to 900 nm, and more preferably, 630 nm to 800 nm.

The present invention further provides an application of the above metal complex in an organic optoelectronic device, and the organic optoelectronic device includes organic light-emitting devices (OLEDs), organic thin film transistors (OTFTs), organic photovoltaics (OPVs), luminescent electrochemical cells (LECs) and chemical sensors, preferably, OLEDs.

Provided is an organic light-emitting device (OLEDs) containing the above metal complex; and the complex serves as a light-emitting material in a light-emitting device.

The organic light-emitting device of the present invention includes a cathode, an anode, and an organic layer, where the organic layer is one or more of a hole injection layer, a hole transport layer, a light-emitting layer, a hole blocking layer, an electron injection layer and an electron transport layer; and it is unnecessary to provide each of these organic layers.

At least one of the hole injection layer, the hole transport layer, the hole blocking layer, the light-emitting layer and/or the electron transport layer contains the compound of Formula (I).

Preferably, the compound of structural formula (I) is located at the light-emitting layer or the electron transport layer.

The device of the present invention has a total thickness of organic layers of 1-1000 nm, preferably, 1-500 nm, more preferably, 5-300 nm.

The organic layers may form a film via evaporation or a solution method.

The present invention has the following beneficial effects: (1) the metal complex of the present invention is applied in OLED devices to have good performance of a device; and the luminous efficiency is improved greatly, and the service life of a device can be promoted obviously; (2) when the conventional light-emitting molecules are in the state of aggregation, stronger intermolecular interaction leads to reduced luminescence quantum yield; while the metal complex of the present invention has the property of aggregation-induced emission enhancement when in the state of aggregation, thus being beneficial to improving the luminous efficiency of a device.

BRIEF DESCRIPTION OF DRAWINGS

FIGURE is a structure diagram showing an organic light-emitting device of the present invention;

10 represents glass substrate; 20 represents anode; 30 represents hole injection layer; 40 represents hole transport layer; 50 represents light-emitting layer; 60 represents hole blocking layer; 70 represents electron transport layer; 80 represents electron injection layer; 90 represents cathode.

DETAILED DESCRIPTION OF EMBODIMENTS

The synthesis method of the material is not required in this present invention. To describe the present invention specifically, examples are set forth below, but not limited thereto.

Raw materials of the compound of the following formula are commercially available.

Example 1

Synthesis of the Complex 4

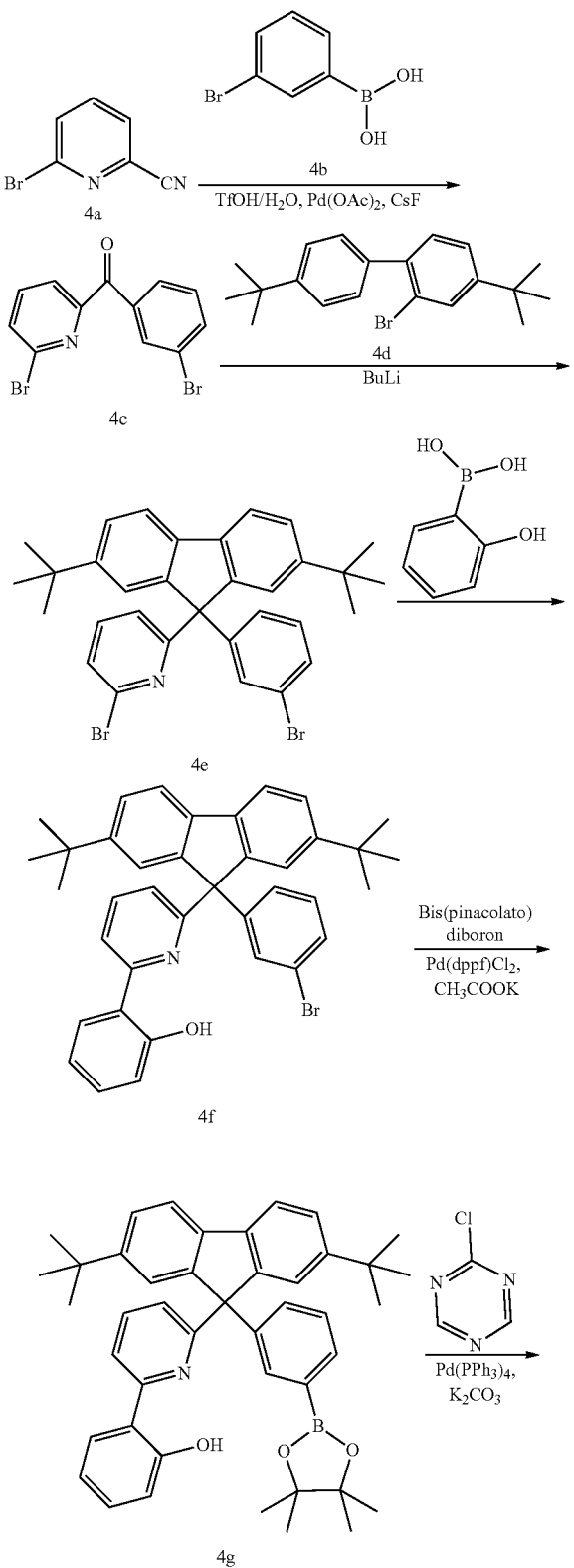

-continued

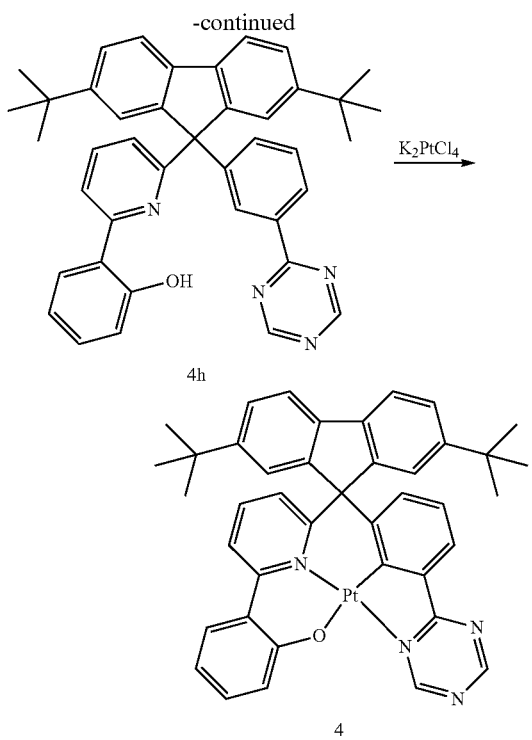

Synthesis of the Intermediate 4c

The compound 4a (3.5 g, 19.2 mmol), compound 4b (4.6 g, 23.0 mmol), palladium acetate (0.4 g, 0.2 mmol) and CsF (3.0 g, 20.0 mmol) were dissolved into a mixed solution of trifluoromethanesulfonic acid (10 mL) and water (30 mL), and heated up to 60° C. for reaction for 8 h. The above reaction liquid was cooled to room temperature and added to water, then extracted for three times with dichloromethane; organic phases were combined. The organic phase was dried by anhydrous sodium sulfate and subjected to rotary evaporation to remove solvent; the residue was separated by column chromatography to obtain a white solid (4.7 g, yield: 71%). ESI-MS (m/z): 339.9 (M+1). Remarks: the reaction yield reduces significantly when the reaction is amplified.

Synthesis of the Compound 4e

The compound 4c (17.0 g, 50.0 mmol) was dissolved into tetrahydrofuran (100 mL) under the protection of nitrogen, and cooled to −78° C., then dropwisely added with n-butyl-lithium BuLi (1.2 eq), and stirred for 30 min, afterwards, the tetrahydrofuran solution (30 mL) of the compound 4d (17.3 g, 50.0 mmol) was dropwisely added to the above solution, stirred for 30 min, and heated up to room temperature, and stirred for 1 h continuously. The above reaction liquid was added to water and then extracted for three times with dichloromethane; organic phases were combined. The organic phase was dried by anhydrous sodium sulfate and subjected to rotary evaporation to remove solvent, thus obtaining a light yellow solid. The above solid was dissolved into acetic acid (50 mL), and added with concentrated sulfuric acid (4 mL) for reflux over the night under the protection of nitrogen. The above reaction liquid was cooled to room temperature and added to water, then extracted for three times with dichloromethane; organic phases were combined. The organic phase was dried by anhydrous sodium sulfate and subjected to rotary evaporation to remove solvent; the residue was separated by column chromatography to obtain a light yellow solid (18.6 g, yield: 63%). ESI-MS (m/z): 588.1 (M+1).

Synthesis of the Compound 4f

The compound 4e (5.9 g, 10.0 mmol), o-hydroxybenzeneboronic acid (1.6 g, 12.0 mmol), Pd(PPh$_3$)$_4$ (0.6 g, 0.5 mmol), K$_2$CO$_3$ (4.0 g, 30.0 mmol), tetrahydrofuran (50 mL) and water (5 mL) were successively added to a Schlenk tube under the protection of nitrogen. The system was heated up to 80° C. for reaction for 24 h. The above reaction liquid was cooled to room temperature and added to water, then extracted for three times with dichloromethane; organic phases were combined. The organic phase was dried by anhydrous sodium sulfate and subjected to rotary evaporation to remove solvent; the residue was separated by column chromatography to obtain an off white solid (4.9 g, yield: 81%). ESI-MS (m/z): 600.2 (M−1).

Synthesis of the Compound 4g

The compound 4f (4.9 g, 8.1 mmol), bis(pinacolato)diboron (37 mmol, 10.0 mmol), potassium acetate (2.5 g, 25.0 mmol), and Pd(dppf)Cl$_2$ (0.3 g, 0.4 mmol) were dissolved into dioxane (50 mL) under the protection of nitrogen, and replaced by nitrogen for several times, then heated for reflux reaction over the night. The above reaction liquid was cooled to room temperature and added to water, then extracted for three times with ethyl acetate; organic phases were combined. The organic phase was dried by anhydrous sodium sulfate and subjected to rotary evaporation to remove solvent; the residue was separated by column chromatography to obtain an off white solid (4.5 g, yield: 85%). ESI-MS (m/z): 648.4 (M−1).

Synthesis of the Compound 4h

The compound 4g (4.2 g, 6.5 mmol), chloro-s-triazine (1.0 g, 8.5 mmol), Pd(PPh$_3$)$_4$ (0.3 g, 0.3 mmol), K$_2$CO$_3$ (1.3 g, 10.0 mmol), tetrahydrofuran (30 mL) and water (5 mL) were successively added to a Schlenk tube under the protection of nitrogen. The system was heated up to 80° C. for reaction for 24 h. The above reaction liquid was cooled to room temperature and added to water, then extracted for three times with dichloromethane; organic phases were combined. The organic phase was dried by anhydrous sodium sulfate and subjected to rotary evaporation to remove solvent; the residue was separated by column chromatography to obtain a light yellow solid (2.4 g, yield: 62%). ESI-MS (m/z): 601.3 (M−1).

Synthesis of the Complex 4

The compound 4h (2.0 g, 3.3 mmol), potassium chloroplatinate (1.7 g, 4.0 mmol) and 250 mL acetic acid were added to a flask and stirred for 48 h at reflux under the protection of nitrogen. The above reaction liquid was cooled to room temperature, then added to water and filtered to obtain a coarse product, and the coarse product was recrystallized to obtain a red solid (2.4 g, yield: 90%). ESI-MS (m/z): 796.3 (M+1).

Example 2

Synthesis of the Complex 29

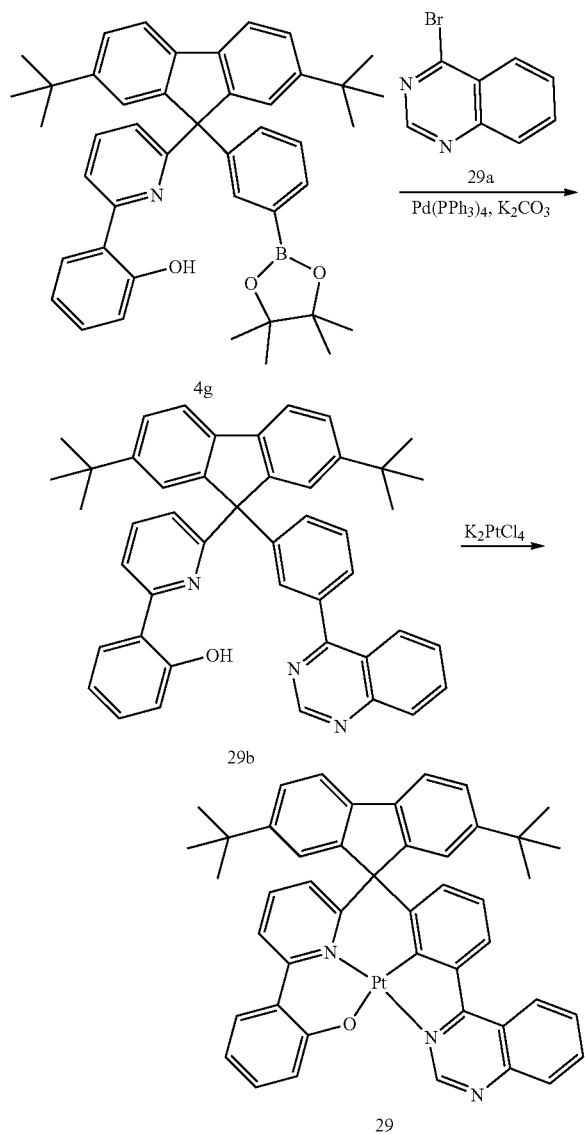

Example 3

Synthesis of the Complex 32

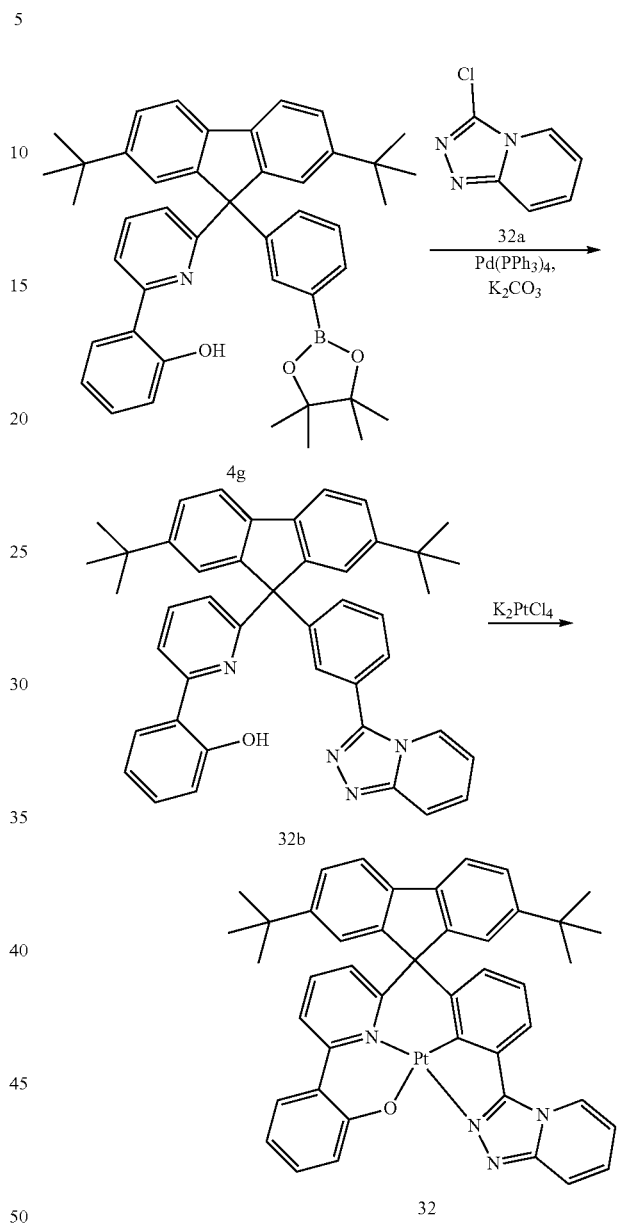

Synthesis of the Compound 29b

The intermediate chloro-s-triazine was replaced with an intermediate 29a and the compound 29b was prepared by reference to the synthesis method of the compound 4h to obtain a light yellow solid (3.2 g, yield: 70%) ESI-MS (m/z): 650.3 (M−1).

Synthesis of the Complex 29

The intermediate 4h was replaced with an intermediate 29b and the compound complex 29 was prepared by reference to the synthesis method of the complex 4 to obtain a red solid (2.9 g, yield: 85%) ESI-MS (m/z): 845.3 (M+1).

Synthesis of the Compound 32b

The intermediate chloro-s-triazine was replaced with an intermediate 32a and the compound 32b was prepared by reference to the synthesis method of the compound 4h to obtain a light yellow solid (2.1 g, yield: 55%) ESI-MS (m/z): 639.3 (M−1).

Synthesis of the Complex 32

The intermediate 4h was replaced with an intermediate 32b and the compound complex 32 was prepared by reference to the synthesis method of the complex 4 to obtain a red solid (2.3 g, yield: 81%) ESI-MS (m/z): 834.3 (M+1).

Example 4

Synthesis of the Complex 36

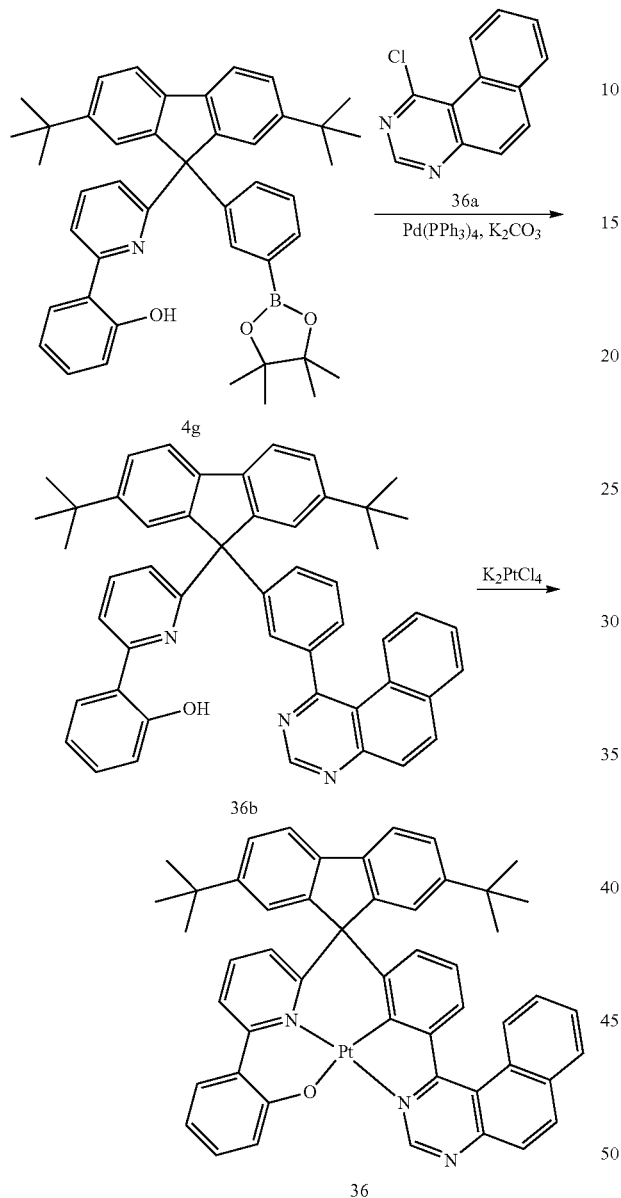

Synthesis of the Compound 36b

The intermediate chloro-s-triazine was replaced with an intermediate 32a and the compound 32b was prepared by reference to the synthesis method of the compound 4h to obtain a light yellow solid (2.1 g, yield: 55%)ESI-MS (m/z): 700.3 (M−1).

Synthesis of the Complex 36

The intermediate 4h was replaced with an intermediate 36b and the compound complex 36 was prepared by reference to the synthesis method of the complex 4 to obtain a red solid (1.9 g, yield: 65%)ESI-MS (m/z): 895.5 (M+1).

Example 5

Synthesis of the Complex 54

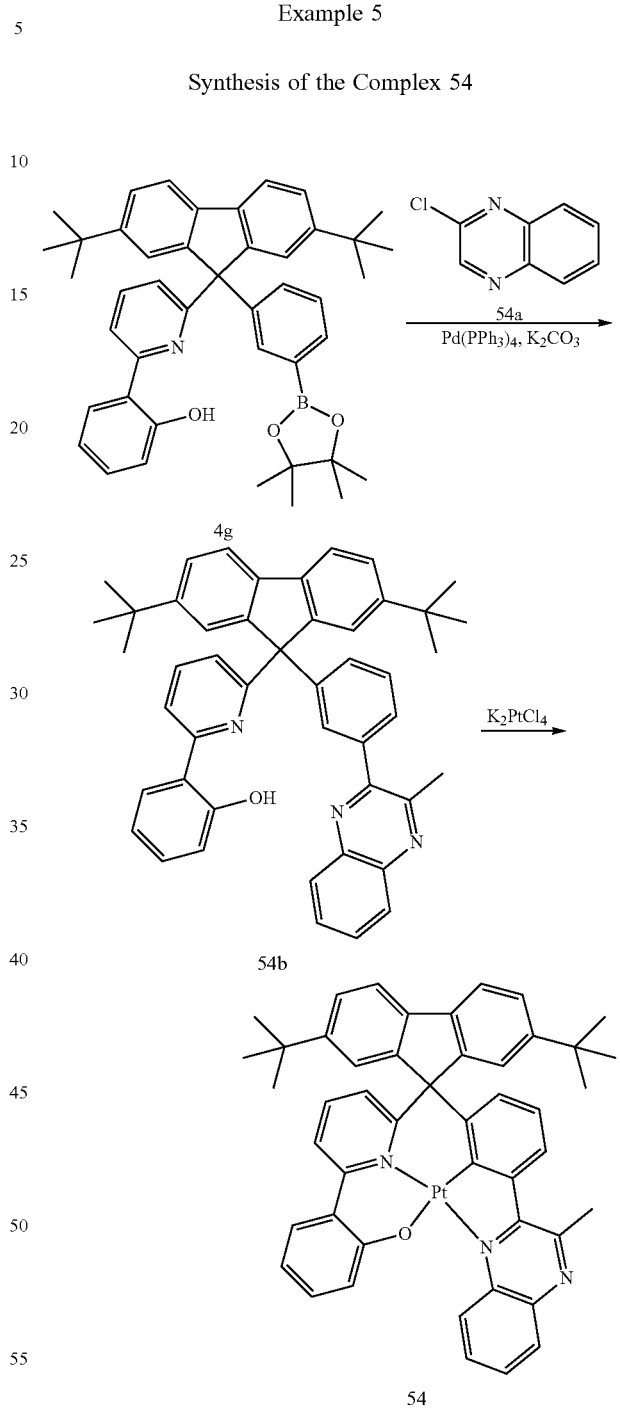

Synthesis of the Compound 54b

The intermediate chloro-s-triazine was replaced with an intermediate 54a and the compound 54b was prepared by reference to the synthesis method of the compound 4h to obtain a light yellow solid (3.5 g, yield: 69%)ESI-MS (m/z): 664.4 (M−1).

Synthesis of the Complex 54

The intermediate 4h was replaced with an intermediate 54b and the compound complex 54 was prepared by reference to the synthesis method of the complex 4 to obtain a red solid (1.3 g, yield: 81%)ESI-MS (m/z): 859.2 (M+1).

Examples 6-10

A light-emitting device was prepared by using the complex light-emitting material of the present invention, and the device has a structure shown in the FIGURE.

Firstly, a transparent conductive ITO glass substrate 10 (an anode 20 was provided) was successively cleaned with a detergent solution and deionized water, ethanol, acetone, and deionized water, and then subjected to plasma treatment with oxygen for 30 s.

HATCN having a thickness of 10 nm was then evaporated on the ITO as a hole injection layer 30.

A compound NPB was then evaporated to form a hole transport layer 40 having a thickness of 40 nm.

A light-emitting layer 50 having a thickness of 20 nm was then evaporated on the hole transport layer; the light-emitting layer was obtained by mixing and doping the complex 4 (Example 6) in Examples 1-5, complex 29 (Example 7), complex 32 (Example 8), complex 36 (Example 9), or complex 54 (Example 10) with CBP (95%) respectively.

Alq having a thickness of 10 nm was then evaporated on the light-emitting layer as a hole blocking layer 60, then, $Alq_3$ having a thickness of 40 nm was evaporated on the hole blocking layer as an electron transport layer 70.

Finally, 1 nm LiF was evaporated as an electron injection layer 80 and 100 nm Al was evaporated as a cathode 90 of the device.

Comparative Example

The compound of the present invention was replaced with $(pq)_2Ir(acac)$ to prepare the organic light-emitting device according to the same method.

HATCN, NPB, CBP, $(pq)_2Ir(acac)$, $Alq_3$ and BAlq in the device have the following structural formulas:

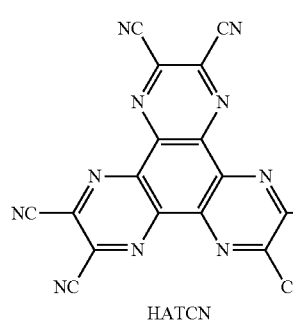

HATCN

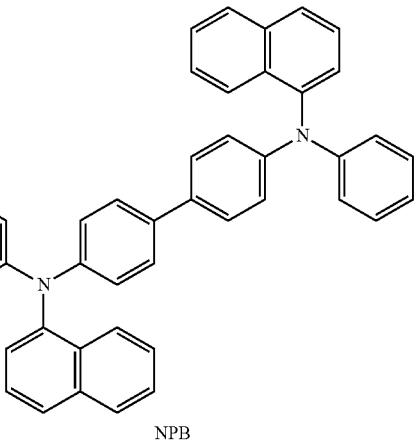

NPB

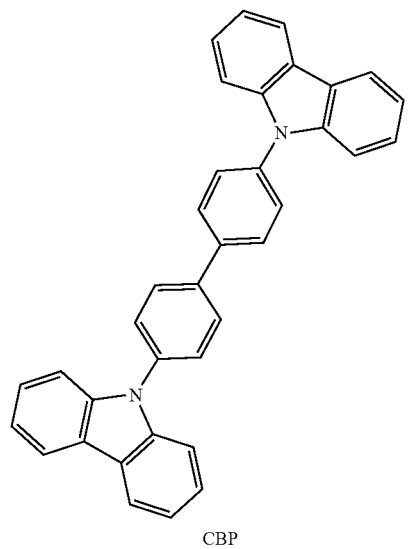

CBP

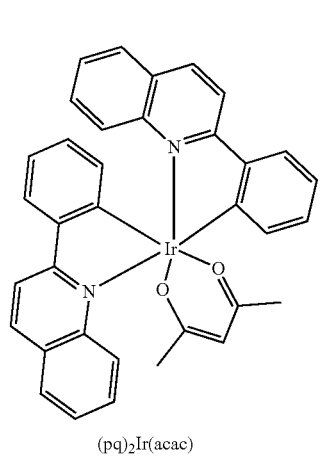

$(pq)_2Ir(acac)$

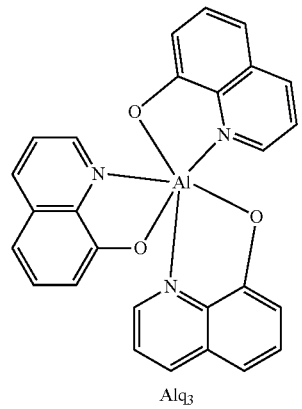

$Alq_3$

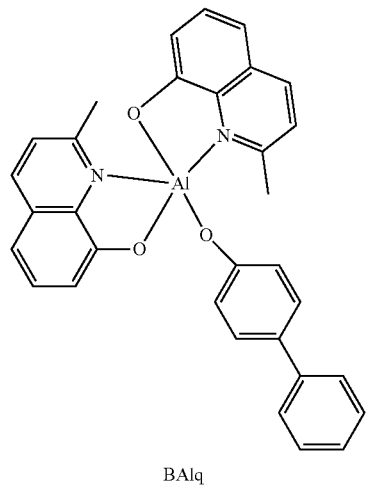

BAlq

Performance of the organic electroluminescent devices in Examples 6-10 and Comparative Example at an electric current density of 10 mA/cm² is listed in Table 1:

TABLE 1

| Example | Compound | Driving voltage | Luminous efficiency | Device service life (LT90) | Emitting color |
|---|---|---|---|---|---|
| 6 | 4 | 0.83 | 1.6 | 2.1 | Dark red light |
| 7 | 29 | 0.83 | 1.3 | 2.0 | Dark red light |
| 8 | 32 | 0.91 | 1.2 | 1.5 | Dark red light |
| 9 | 36 | 0.76 | 1.3 | 2.1 | Near-infrared light |
| 10 | 54 | 0.82 | 1.4 | 1.6 | Dark red light |
| Comparative Example | (pq)₂Ir(acac) | 1 | 1 | 1 | Red light |

Remarks: the performance test of the device is by reference to the Comparative Example; each index in the Comparative Example is set 1; LT90 shows the corresponding time when the device brightness attenuates to 90% of the initial brightness.

It can be seen from the data of Table 1 that under the same conditions, the efficiency of the organic light-emitting device prepared by the compound of the present invention is superior to that of the Comparative Example; compared with a common red emitting material (pq)₂Ir(acac), the metal complex material of the present invention is applied in an organic light-emitting device to have a lower driving voltage and greatly improved service life, and to emit dark red or near-infrared light, which conforms to the demands of the display industry for light-emitting materials and thus, has good industrialization prospect.

Example 11

Ratio ($\Phi_{PPMA}/\Phi_{solution}$) of luminescence quantum yields of the metal complexes 4, 29, 32, 36 and 54 in the PMMA film and dichloromethane solution is listed in Table 2:

TABLE 2

| | Complex | | | | |
|---|---|---|---|---|---|
| | 4 | 29 | 32 | 36 | 54 |
| $\Phi P_{MMA}/\Phi_{solution}$ | 1.2 | 1.3 | 1.6 | 1.8 | 1.9 |

$\Phi_{PMMA}$: the luminescence quantum yield of the complex doped in PMMA(20%); $\Phi_{solution}$: the luminescence quantum yield of the complex doped in dichloromethane solution (1 × 10⁻⁵M).

It can be seen from the data of Table 2 that the quantum yield of the metal complex of the present invention in the state of aggregation is higher than that in solution. Due to the concentration quenching effect, the luminescence quantum yield of the platinum complex material is usually lower under the state of aggregation. The metal complex of the present invention shows the property of aggregation-induced emission enhancement. As can be seen, the present invention achieves unexpected technical effect.

The above multiple embodiments are merely set as examples, but are not construed as limiting the protection scope of the present invention. Multiple materials and structures of the present invention may be replaced by other materials and structures in the premise of not departing from the spirit of the present invention. It should be understood that a person skilled in the art can make lots of modifications and changes according to the idea of the present invention without inventive efforts. Therefore, any technical solution obtained by a person skilled in the art on the basis of the prior art and through analysis, reasoning or partial researches shall fall within the protection scope defined in the claims.

The invention claimed is:

1. A metal complex, being a compound having a structure as shown in Formula (I):

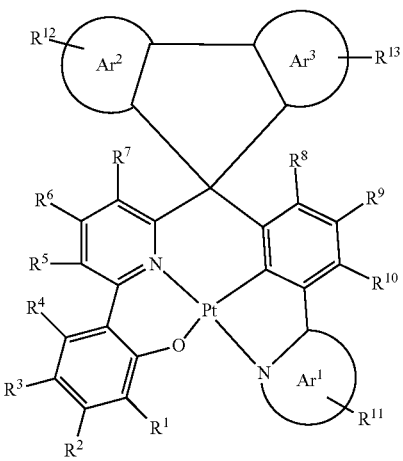

wherein:
$R^1, R^2, R^3, R^4, R^5, R^6, R^7, R^8, R^9, R^{10}, R^{11}, R^{12}$ and $R^{13}$ are each independently selected from:
hydrogen,
deuterium,
halogen,
substituted or unsubstituted alkyl having 1-20 carbon atoms,
substituted or unsubstituted cycloalkyl having 3-20 carbon atoms,
substituted or unsubstituted alkoxy having 1-20 carbon atoms,
substituted or unsubstituted aryl having 6-30 carbon atoms,
substituted or unsubstituted heteroaryl having 3-30 carbon atoms, and
cyano;
$Ar^1$ is a heteroaromatic group containing at least two N atoms and 3-30 carbon atoms;
$Ar^2$ and $Ar^3$ are each independently selected from an aromatic group or a heteroaromatic group having 3-30 carbon atoms;
heteroatom in the heteroaromatic group is selected from atoms N, S, O; and
the substitution refers to a substitution by deuterium, halogen or alkyl having 1-8 carbon atoms.

2. The metal complex according to claim 1, wherein:
in the Formula (I), $R^1, R^2, R^3, R^4, R^5, R^6, R^7, R^8, R^9, R^{10}, R^{11}, R^{12}$ and $R^{13}$ are respectively selected from:
hydrogen,
deuterium,
halogen,
substituted or unsubstituted alkyl having 1-6 carbon atoms,
substituted or unsubstituted cycloalkyl having 3-6 carbon atoms,
substituted or unsubstituted alkoxy having 1-6 carbon atoms,
substituted or unsubstituted aryl having 6-12 carbon atoms,
substituted or unsubstituted heteroaryl having 3-12 carbon atoms, and
cyano;
$Ar^1$ is a heteroaromatic group containing 2-4 heteroatoms and 3-12 carbon atoms;
$Ar^2$ and $Ar^3$ are each independently selected from an aromatic group or a heteroaromatic group having 3-12 carbon atoms;
heteroatom in the heteroaromatic group is selected from atoms N, S, O; and
the substitution refers to a substitution by deuterium or alkyl having 1-4 carbon atoms.

3. The metal complex according to claim 2, wherein:
in the Formula (I), $R^1, R^2, R^3, R^4, R^5, R^6, R^7, R^8, R^9, R^{10}, R^{11}, R^{12}$ and $R^{13}$ are respectively selected from:
hydrogen,
deuterium,
substituted or unsubstituted alkyl having 1-4 carbon atoms, and
substituted or unsubstituted cycloalkyl having 3-6 carbon atoms; and
$Ar^2$ and $Ar^3$ are each independently selected from an aromatic group or a heteroaromatic group having 5-10 carbon atoms.

4. The metal complex according to claim 3, wherein the $Ar^1$ is selected from the following aromatic structures:

  HA1

  HA2

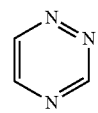  HA3

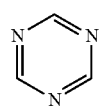  HA4

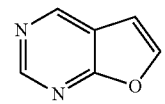  HA5

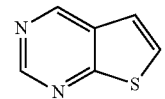  HA6

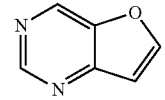  HA7

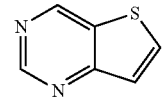  HA8

HA9 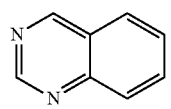

HA10 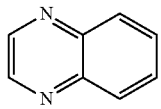

HA11 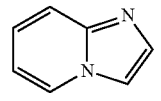

HA12 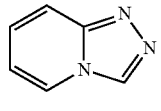

HA13 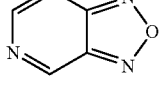

HA14 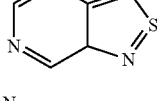

HA15 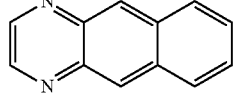

HA16 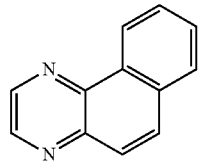

HA17 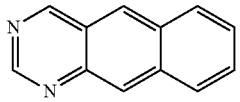

HA18 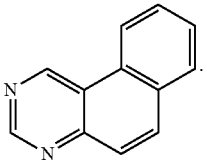

5. The metal complex according to claim 4, wherein the Ar$^1$ is selected from the following aromatic structures:

HA5 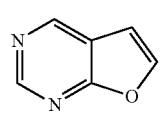

HA6 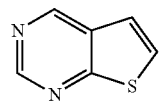

HA7 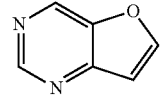

HA8 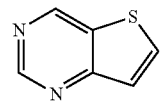

HA9 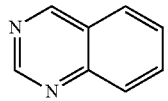

HA10 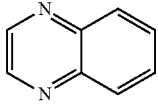

HA11 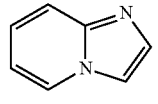

HA12 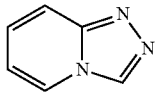

HA13 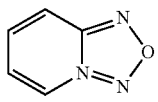

HA14 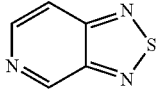

HA15 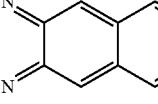

HA16 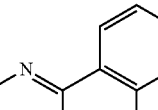

HA17 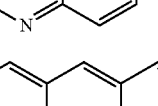

HA18

6. The metal complex according to claim 1, wherein Ar$^2$ and Ar$^3$ are the same aromatic group.

7. The metal complex according to claim 6, wherein the Ar$^2$ and the Ar$^3$ are selected from a benzene or naphthalene unit group.

8. The metal complex according to claim 7, wherein:
 $R^1$, $R^2$, $R^3$, $R^4$, $R^5$, $R^6$, $R^7$, $R^8$, $R^9$ and $R^{10}$ are hydrogen; and
 the $Ar^2$ and the $Ar^3$ are benzene.
9. The metal complex according to claim 1, having one of the following structural formulas:
1
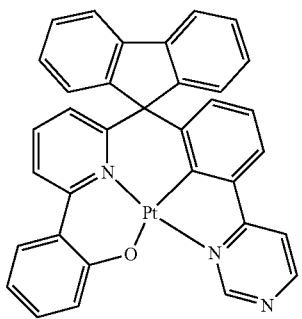
2
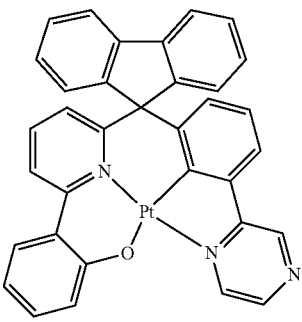
3
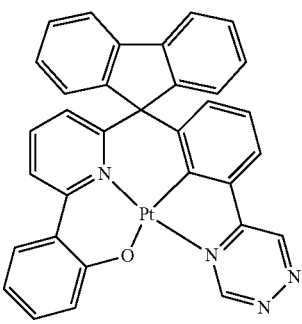
4
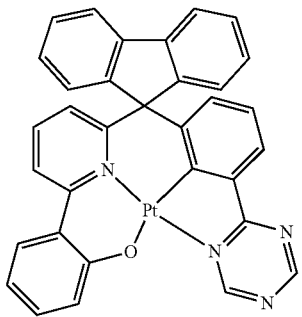
-continued
5
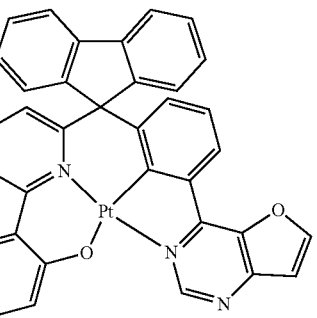
6
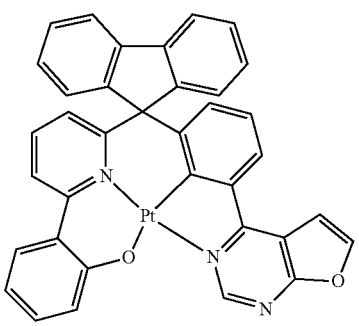
7
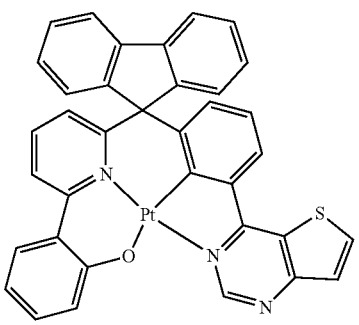
8
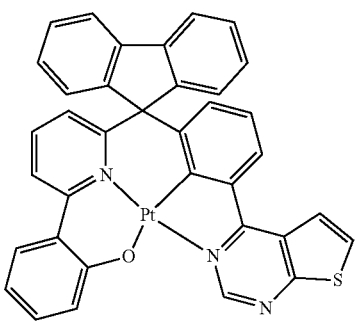
9
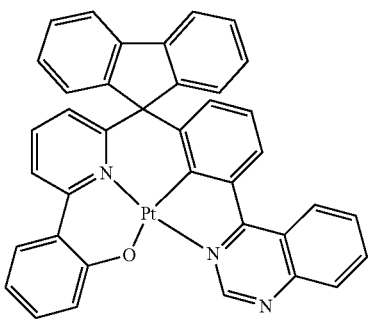

10
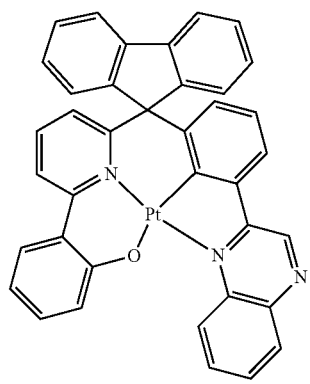
11
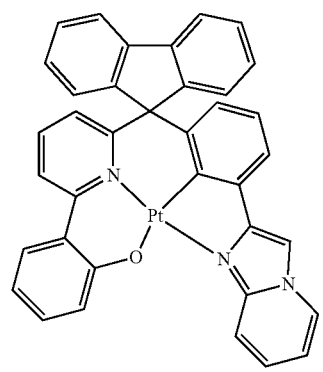
12
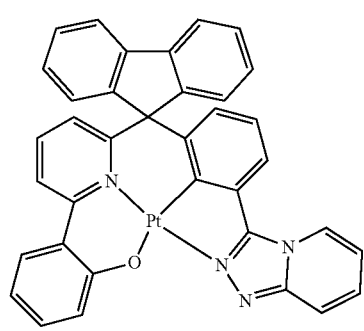
13
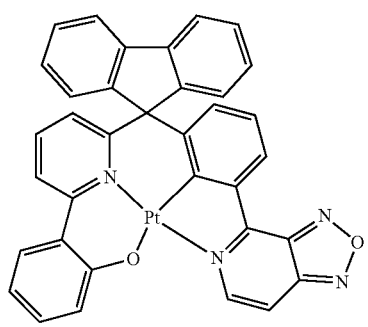
14
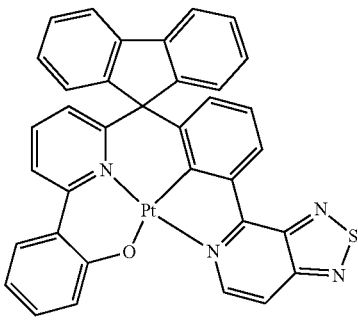
15
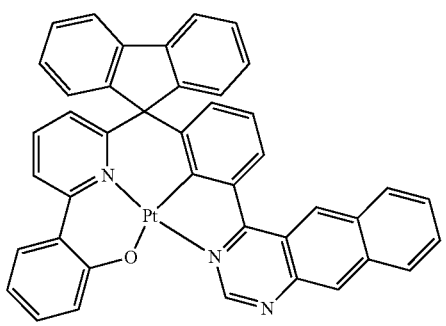
16
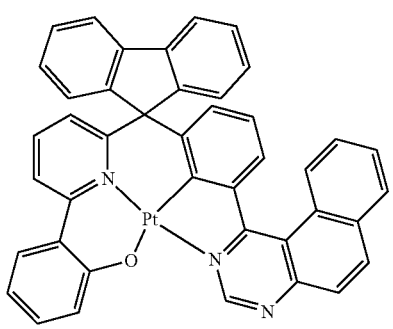
17
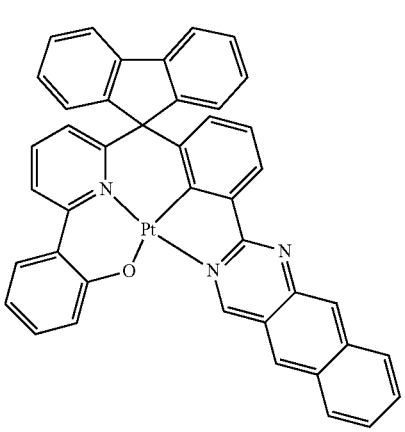

18
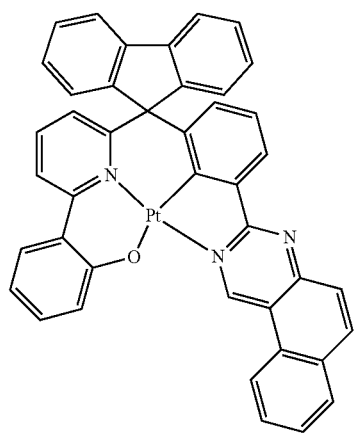
19
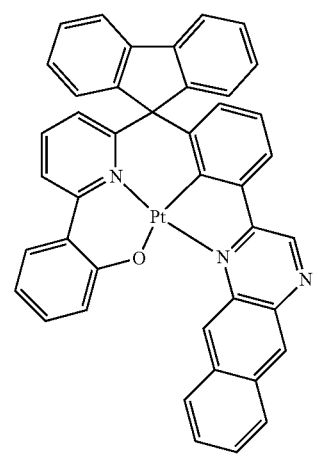
20
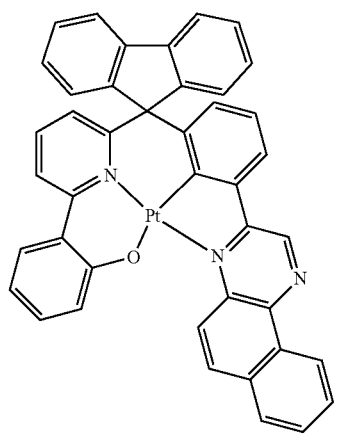
21
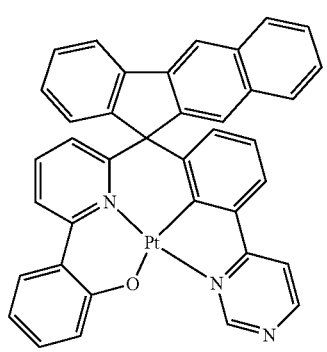
22
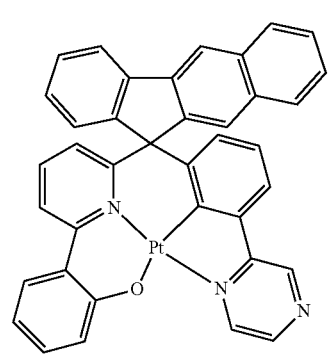
23
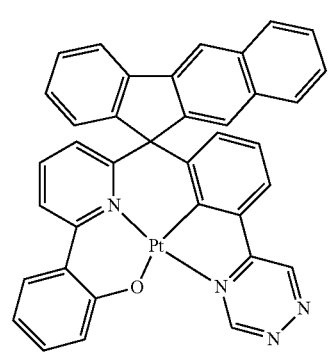
24
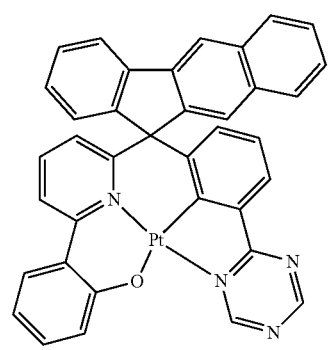
25
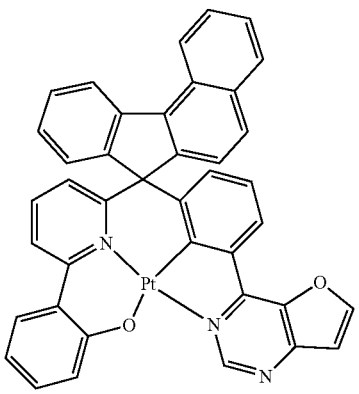

-continued
26
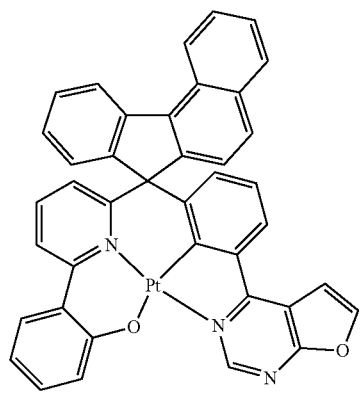
27
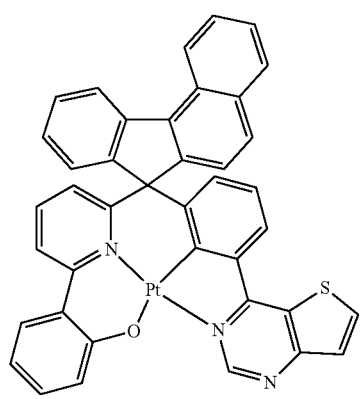
28
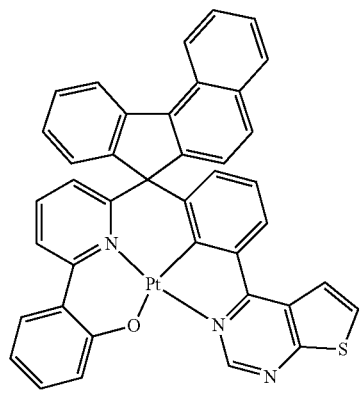
29
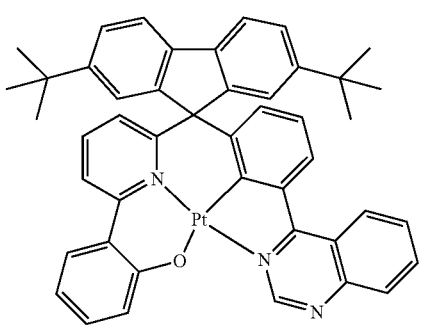
-continued
30
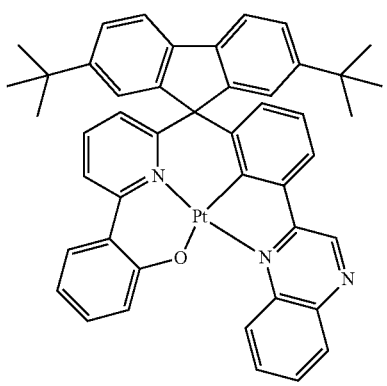
31
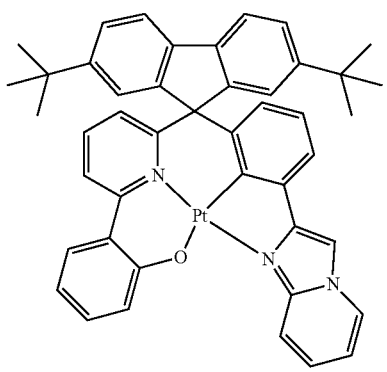
32
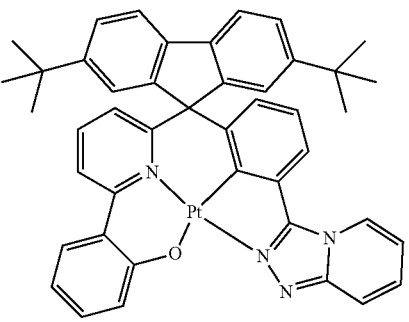
33
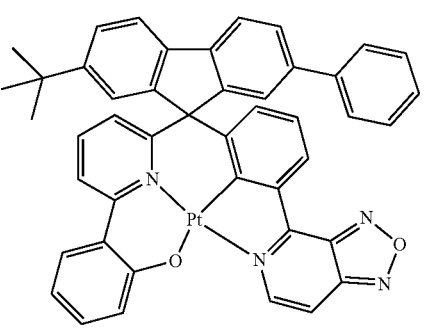

34
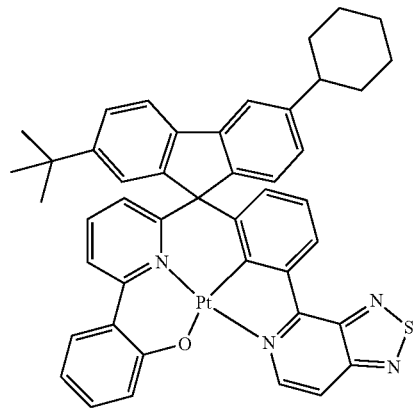
35
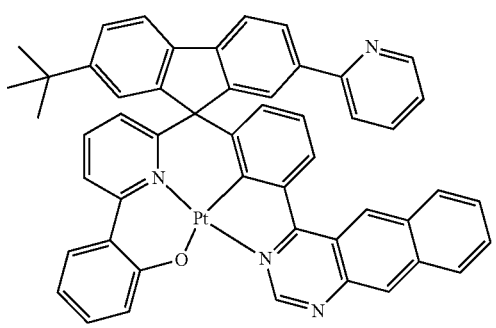
36
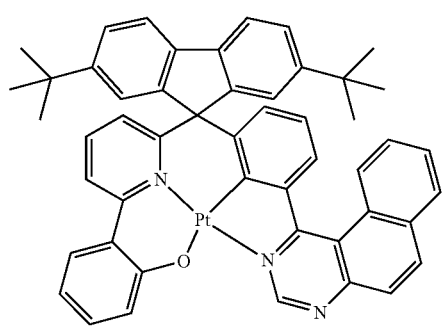
37
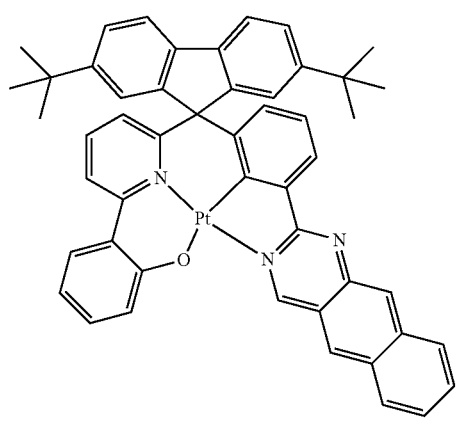
38
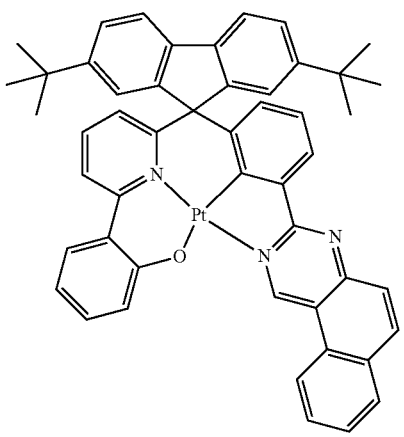
39
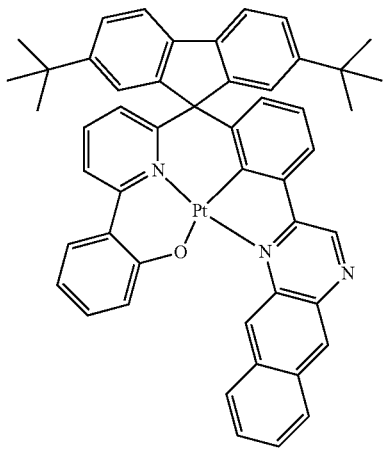
40
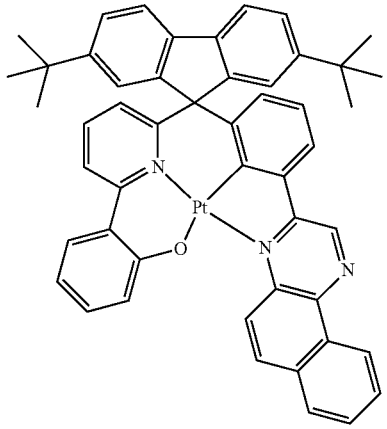
41
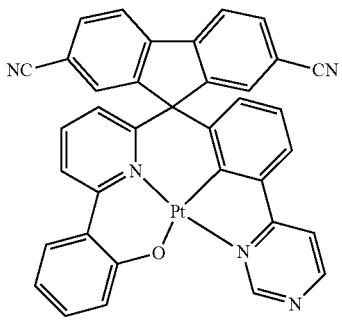

42
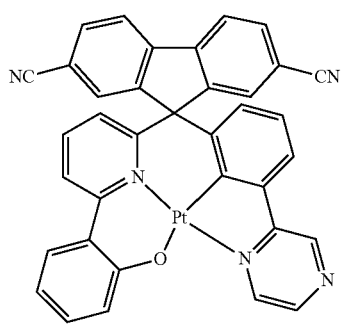
43
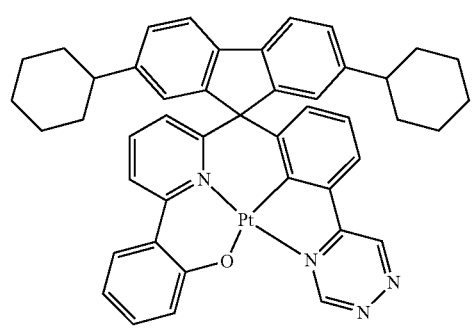
44
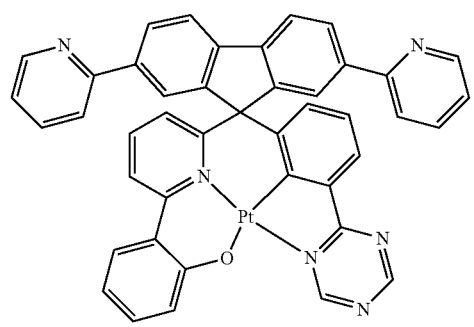
45
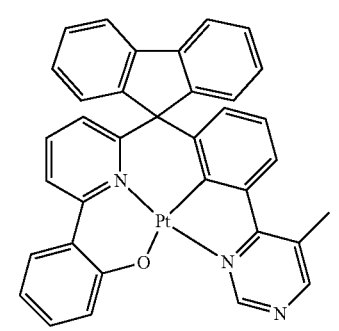
46
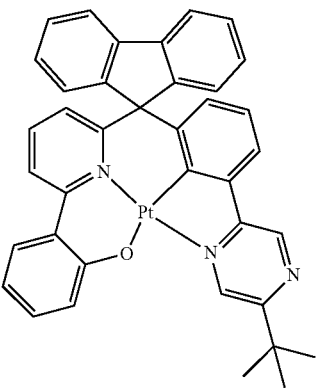
47
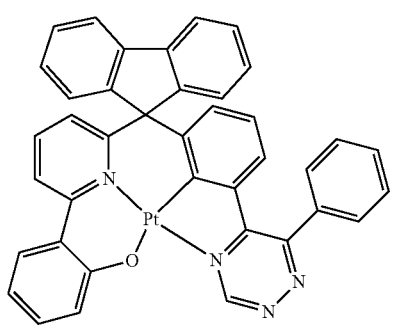
48
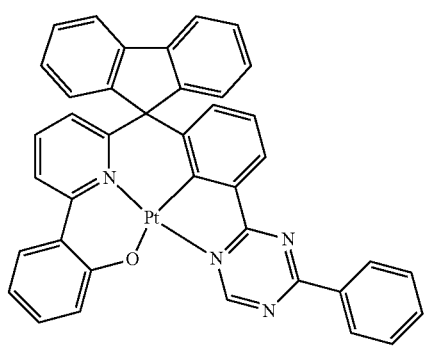
49
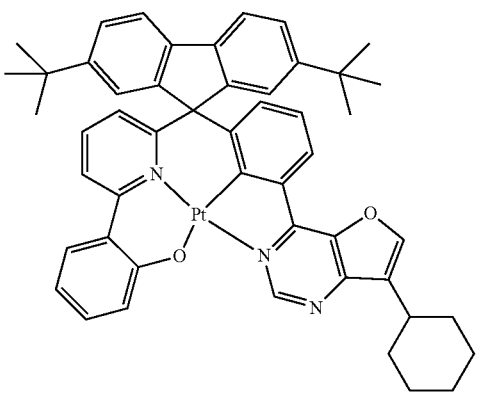

50
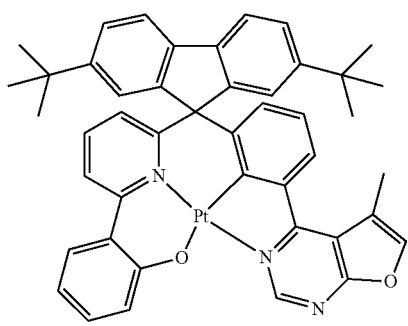
51
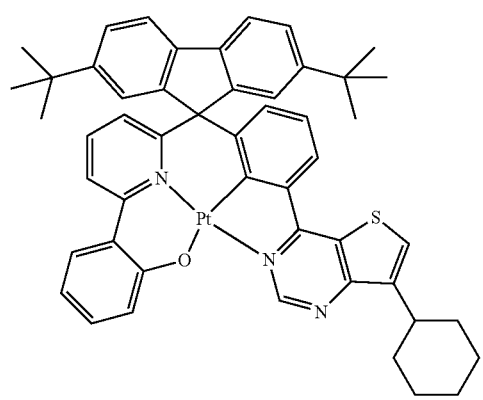
52
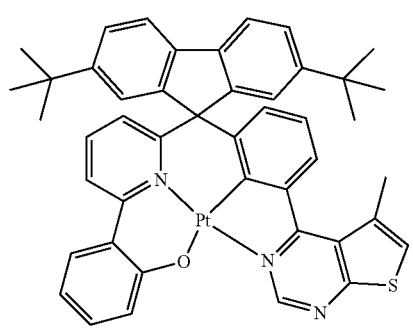
53
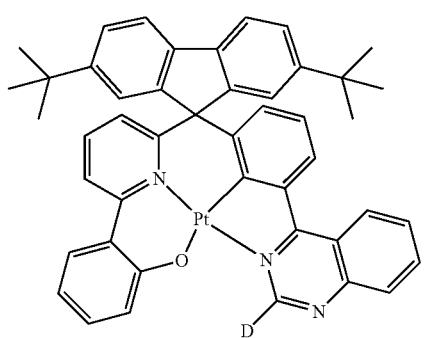
54
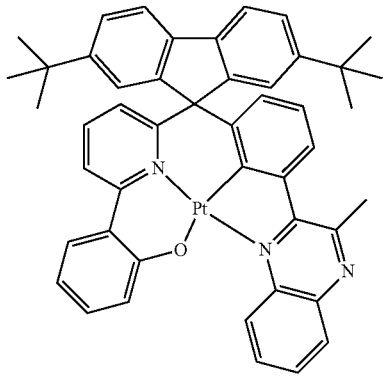
55
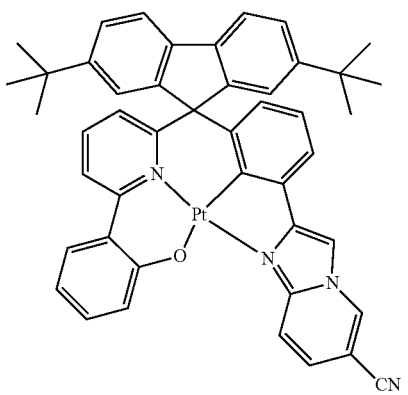
56
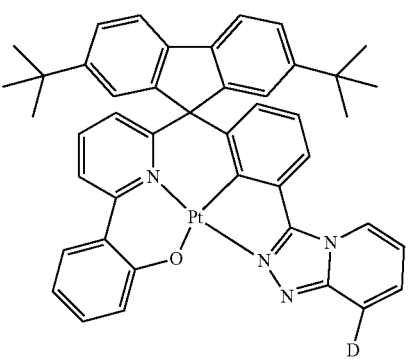
57
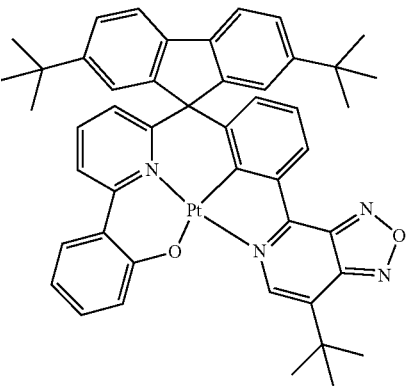

-continued
58
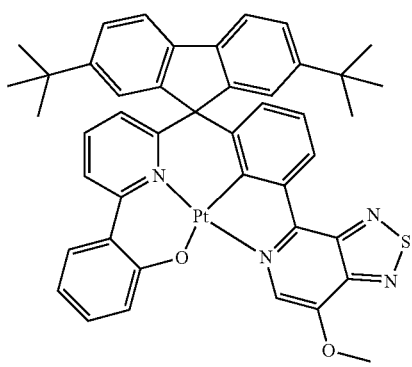
59
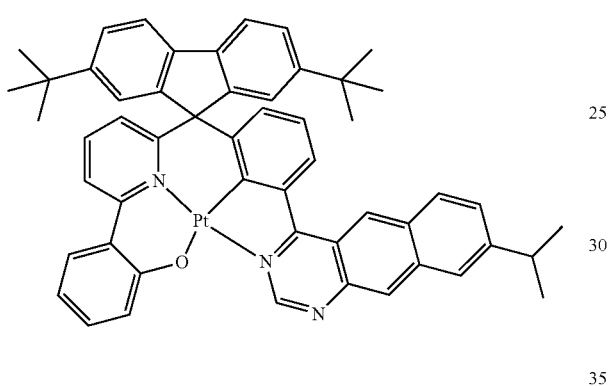
60
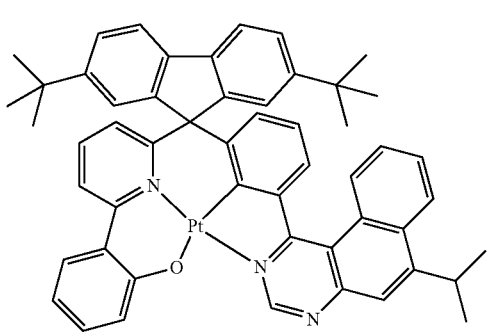
61
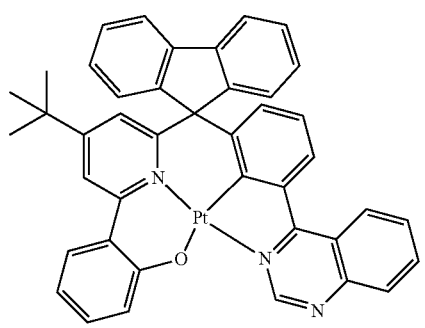
-continued
62
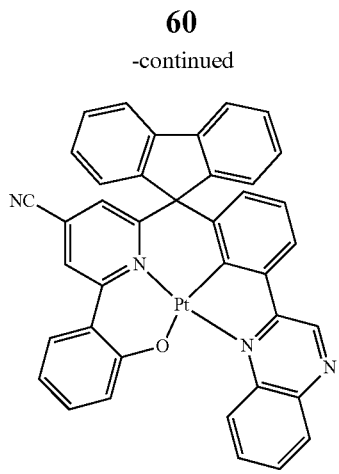
63
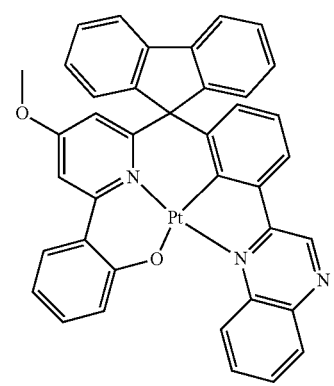
64
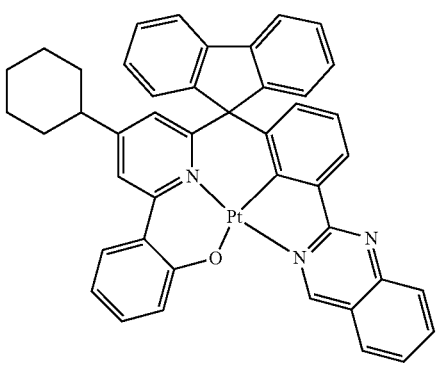
65
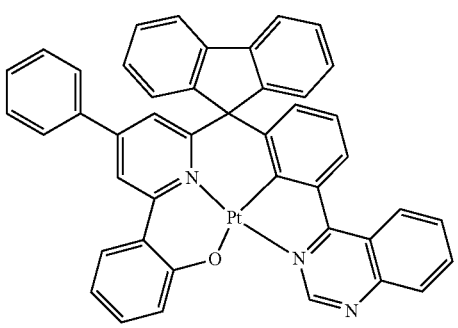

66
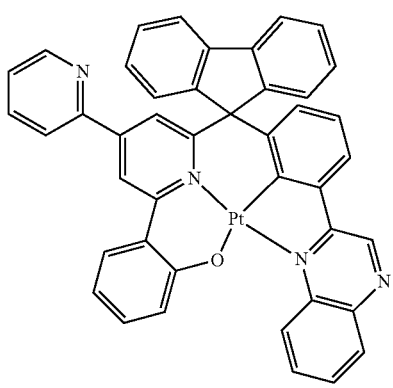
70
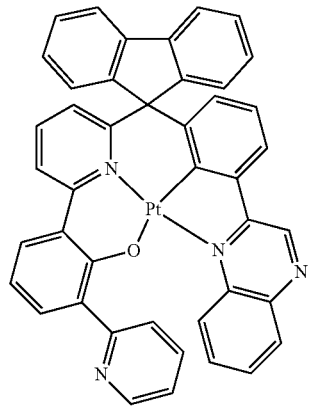
67
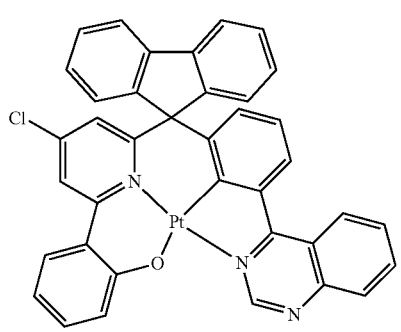
71
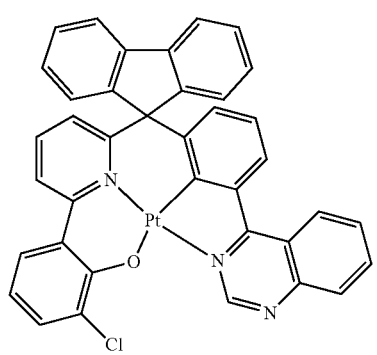
68
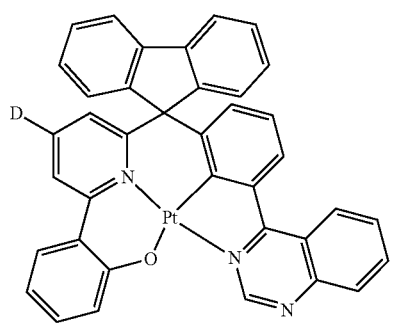
72
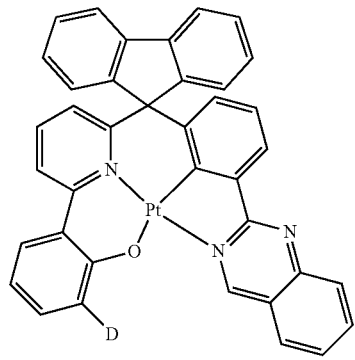
69
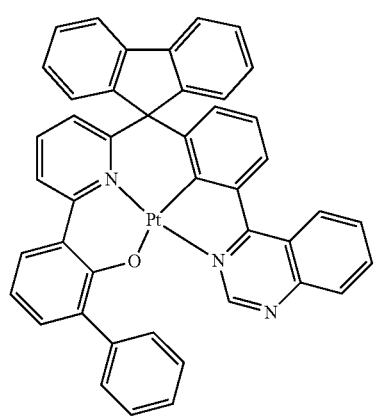
73
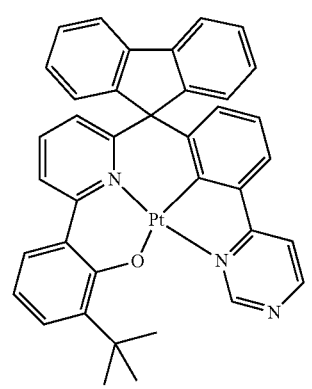

74
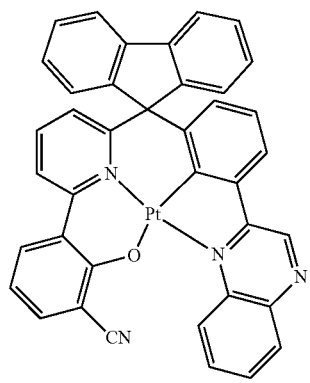
75
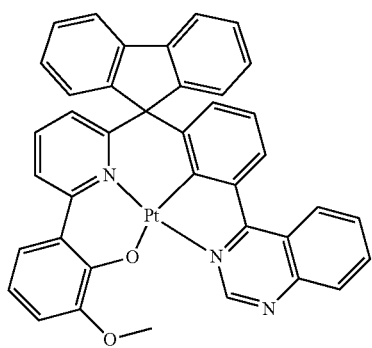
76
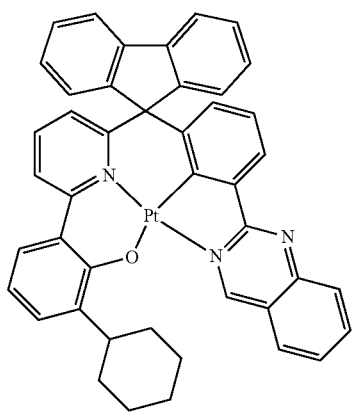
77
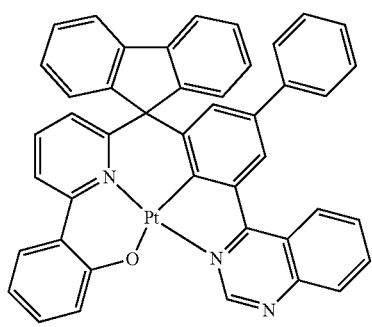
78
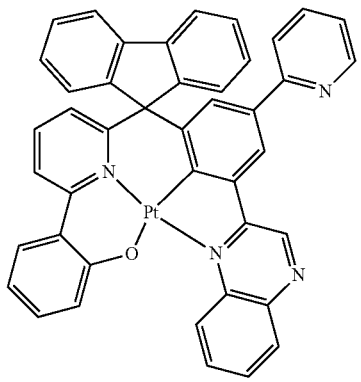
79
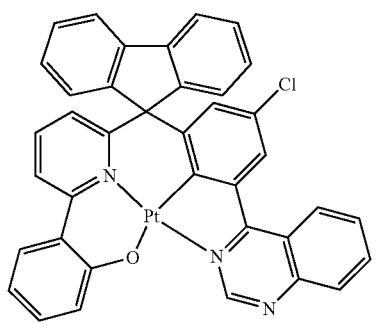
80
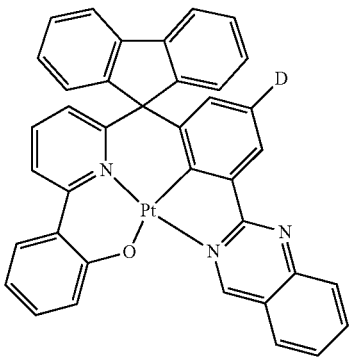
81
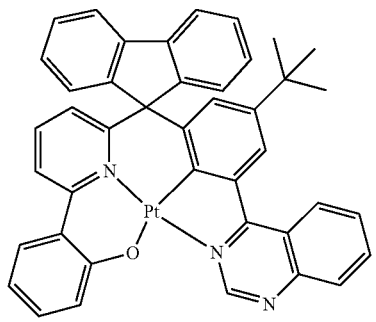

82
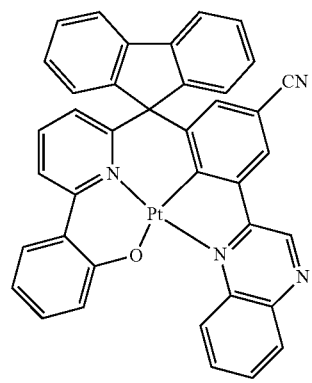
83
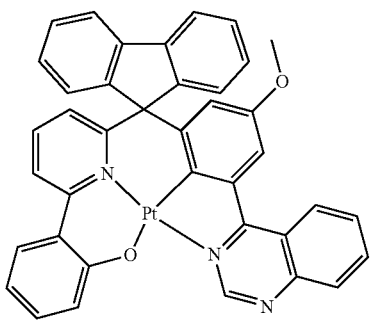
84
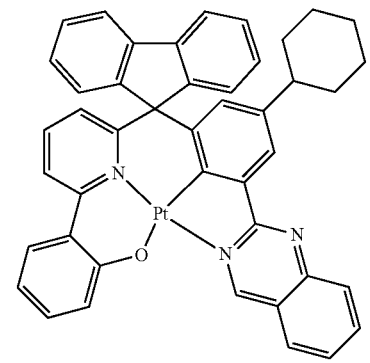
85
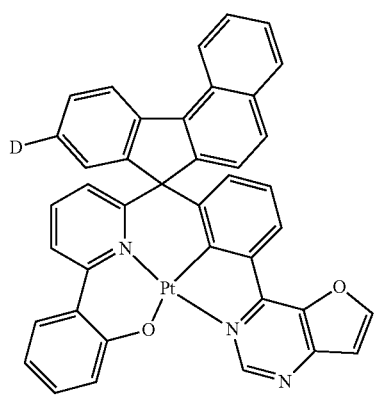
86
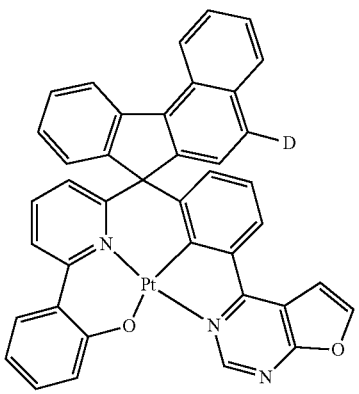
87
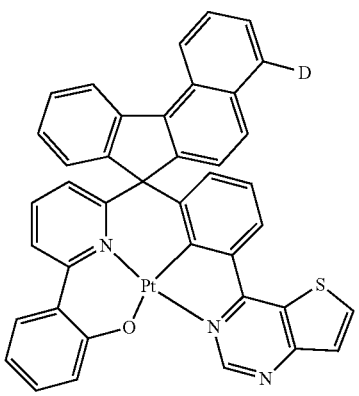
88
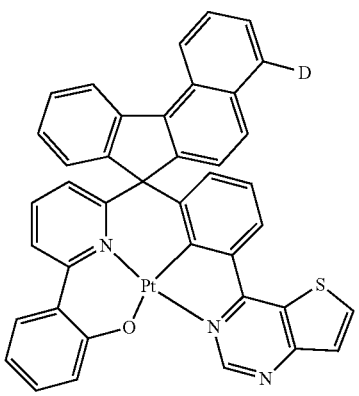
89
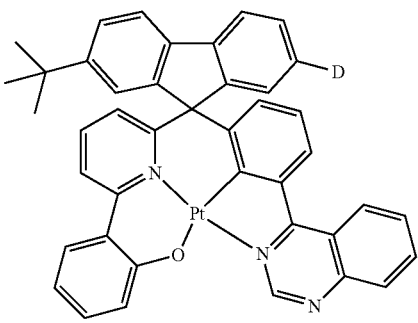

-continued

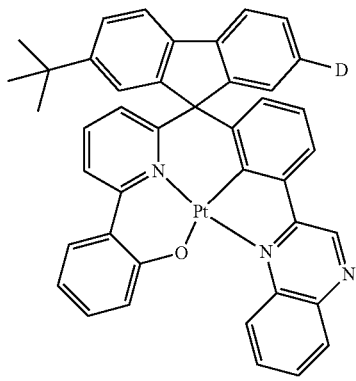

90

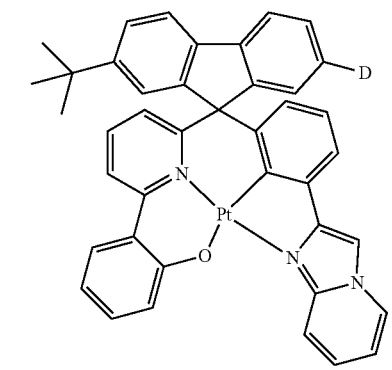

91

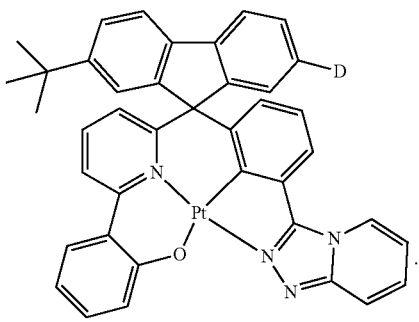

92

10. A precursor of the metal complex according to claim 1, namely, a ligand, having the following structural formula:

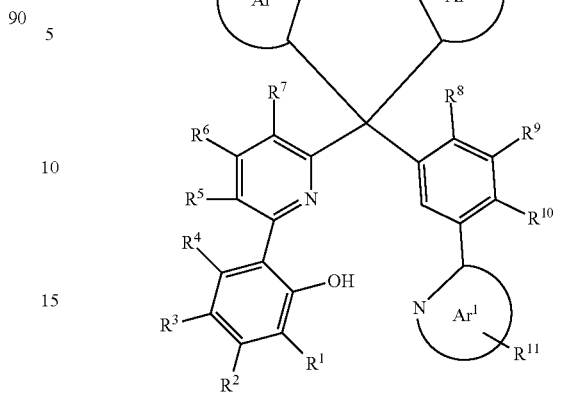

11. An application of the metal complex of claim 1 in an organic optoelectronic device, wherein the organic optoelectronic device comprises:
   an organic light-emitting device,
   an organic thin film transistor,
   an organic photovoltaic device,
   a luminescent electrochemical cell, and
   a chemical sensor.

12. An organic light-emitting device, comprising:
   a cathode,
   an anode, and
   an organic layer,
   wherein:
      the organic layer is one or more of a hole injection layer, a hole transport layer, a light-emitting layer, a hole blocking layer, an electron injection layer and an electron transport layer; and
      the organic layer comprises the metal complex of claim 1.

13. The organic light-emitting device according to claim 12, wherein the metal complex of is located at the light-emitting layer and the electron transport layer.

14. The organic light-emitting device according to claim 12, wherein:
   the organic layer has a total thickness of 1-1000 nm; and
   the organic layer forms a thin film via evaporation or a solution method.

15. The metal complex according to claim 2, wherein $Ar^2$ and $Ar^3$ are the same aromatic group.

16. The metal complex according to claim 3, wherein $Ar^2$ and $Ar^3$ are the same aromatic group.

17. The metal complex according to claim 4, wherein $Ar^2$ and $Ar^3$ are the same aromatic group.

18. The metal complex according to claim 5, wherein $Ar^2$ and $Ar^3$ are the same aromatic group.

19. An organic light-emitting device, comprising:
   a cathode,
   an anode, and
   an organic layer,
   wherein:
      the organic layer is one or more of a hole injection layer, a hole transport layer, a light-emitting layer, a hole blocking layer, an electron injection layer and an electron transport layer; and
      the organic layer comprises the metal complex of claim 2.

20. An organic light-emitting device, comprising:
a cathode,
an anode, and
an organic layer,
wherein:
   the organic layer is one or more of a hole injection layer, a hole transport layer, a light-emitting layer, a hole blocking layer, an electron injection layer and an electron transport layer; and
   the organic layer comprises the metal complex of claim 9.

* * * * *